(12) United States Patent
Polo

(10) Patent No.: US 8,585,727 B2
(45) Date of Patent: Nov. 19, 2013

(54) TISSUE SEVERING DEVICES AND METHODS

(76) Inventor: Oscar R. Polo, Portland, OR (US)

( * ) Notice: Subject to any disclaimer, the term of this patent is extended or adjusted under 35 U.S.C. 154(b) by 0 days.

(21) Appl. No.: 13/495,023

(22) Filed: Jun. 13, 2012

(65) Prior Publication Data

US 2013/0018402 A1    Jan. 17, 2013

Related U.S. Application Data

(63) Continuation of application No. PCT/US2010/024210, filed on Feb. 14, 2010.

(51) Int. Cl.
*A61B 17/32* (2006.01)

(52) U.S. Cl.
USPC .......................................... 606/170; 600/562

(58) Field of Classification Search
USPC .............. 606/80, 159, 167, 170, 171; 604/22; 600/562, 568
See application file for complete search history.

(56) References Cited

U.S. PATENT DOCUMENTS

| 4,574,803 | A | 3/1986 | Storz |
| 5,607,446 | A * | 3/1997 | Beehler et al. ................ 606/198 |
| 6,464,711 | B1 | 10/2002 | Emans et al. |
| 2005/0177168 | A1 | 8/2005 | Brunnett et al. |
| 2008/0249553 | A1 * | 10/2008 | Gruber et al. ................ 606/171 |
| 2010/0082019 | A1 * | 4/2010 | Neev ............................... 606/9 |

FOREIGN PATENT DOCUMENTS

DE    19747149 A1    5/1999

OTHER PUBLICATIONS

International Search Report and Written Opinion for Parent Application PCT/US2010/024210.

\* cited by examiner

*Primary Examiner* — Victor Nguyen
(74) *Attorney, Agent, or Firm* — Silicon Forest Patent Group; Paul J Fordenbacher, Esq

(57) ABSTRACT

Tissue severing devices and methods as provided in embodiments herein are operable to be inserted through small surgical openings and advanced to tissue to be severed. A support ribbon is provided to allow a user to present a cutting element at various angles to an axis of the tissue severing device. The cutting element is exposed by withdrawing a tube member from over the cutting element.

25 Claims, 22 Drawing Sheets

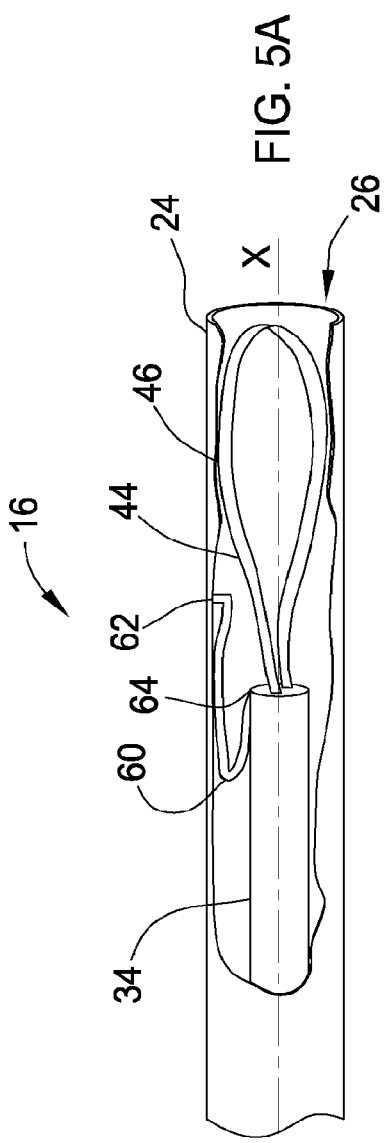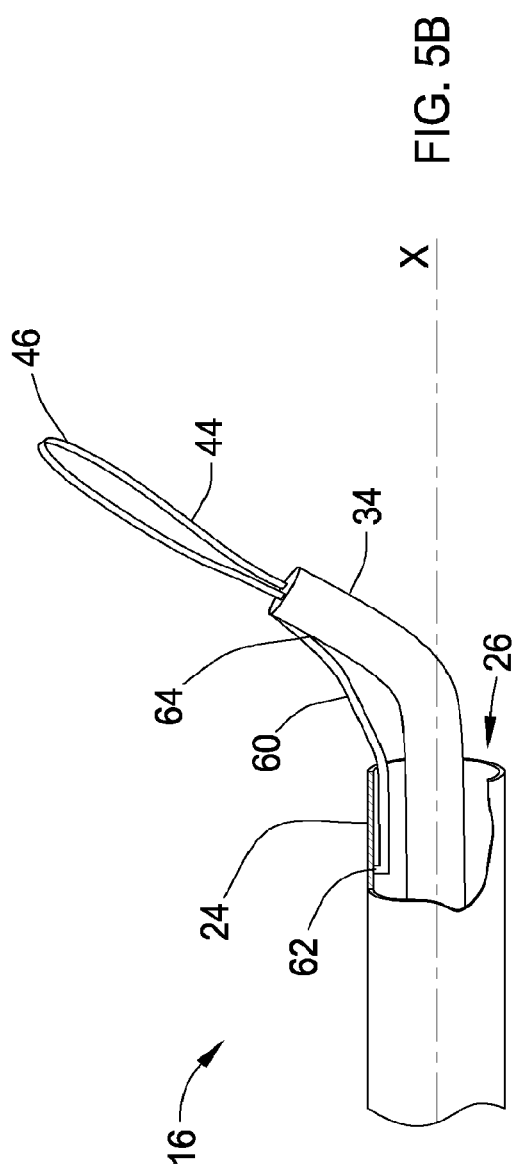

TISSUE SEVERING DEVICES AND METHODS

RELATED APPLICATIONS

This application is a continuation of and claims priority to PCT patent application Serial Number PCT/US10/24210, filed Feb. 14, 2010, entitled TISSUE SEVERING DEVICES AND METHODS, incorporated herein in its entirety by reference.

FIELD

The present invention is related generally to the field of medical devices. More particularly, the present invention involves devices and methods that enable accurate dissection of tissue such as associated with a patient undergoing surgery.

BACKGROUND

During surgical procedures and, more particularly, tissue removal procedures, it is desirable to limit the size of the entry incision to minimize the trauma experienced by the patient. In the past, efforts to minimize entry incision size have generally been limited due to the size of the tissue to be removed and the need for access to the tissue.

However, in modern surgery access to the tissue cite is provided by inserting one or more trocar and cannula. Thereafter, one or more laparoscopes are used to view the tissue to be removed, and additional port sites are used to gain access to the tissue to sever it from tissue which is to remain. However, the entry incision must still be sized to allow removal of the severed tissue and, therefore, the reduction in entry incision size is rather limited even in more modern or recently developed surgical procedures.

Morcellators are devices that morcellate or cut tissue into smaller pieces to allow for easier removal through small surgical access sites. Morcellators that require a pushing or downward traction operation to cut the tissue present a danger of over extension into tissue that is not to be injured. By way of example, but not limited thereto, in a laparoscopic subtotal hysterectomy, one way of minimizing the danger of this over extension is to amputate the body of the uterus from the cervix prior to morcellation. The amputation of the uterus presents an added risk of injury to other organs, such as the rectum and bowel, as they lie behind the uterus and are difficult to see during uterus amputation. Also, amputation is commonly performed using electrocautery or harmonic scalpel which may cause lateral spread of heat or other energy and can inadvertently cause a burn to the bowel or bladder that may not be realized until days after surgery. Further, amputation of the uterus requires the use of one surgical instrument to amputate the uterus and another surgical instrument to morcellate the uterus with their associated cost and complexity of use.

Some known laparoscopic supracervical hysterectomy instruments utilize graspers that pull tissue into a spinning tubular blade or the spinning blade is pushed into the tissue. These types of instruments have their limitations and dangers associated with their use, such as, but not limited to, the exposed sharp blade possibly injuring surrounding tissue not intended to be morcellated, discharge of the tissue in a spinning tool, and the difficulty and dangers of placing downward traction into the target tissue.

There exists a need in the art for surgical devices and methods that allow for more effective tissue severing and morcellating and which allow for morcellation without the need to first amputate the tissue.

SUMMARY

In accordance with an embodiment, a tissue severing device comprises a handle, a tube member, and inner member, and a cutting element. The tube member includes an elongated tube having a tube member proximal end extending into the handle and a tube member distal end opposite the tube member proximal end. The tube member defines a tube member lumen that extends through the tube member proximal end to the tube member distal end and defining a tube member axis. The inner member includes an elongated body having an inner member proximal end extending through the tube member lumen and into the handle and an inner member distal end opposite the inner member proximal end. The inner member is operable to be received within the tube member lumen. The cutting element includes a cutting element proximal end and a cutting element distal end opposite the cutting element proximal end. The cutting element proximal end extends into the inner member distal end. The cutting element distal end extends from the inner member distal end. The tube member distal end is operable to move distally over and receive the inner member distal end and the inner member distal end therein. The tube member distal end is operable to move in a proximal direction to expose the cutting element distal end.

In accordance with another embodiment, the handle further comprises an engagement means in operable engagement with the tube member proximal end operable to permit the tube member to be moved proximally and distally over the inner member.

In accordance with another embodiment, the tissue severing device is operable to present the cutting element distal end at an angle to the tube member axis when the tube member distal end is withdrawn from the cutting element distal end and at least a portion of the inner member distal end.

In accordance with another embodiment, at least a portion of the inner member distal end is biased to form a curve of a predetermined angle with respect to the tube member axis when the tube member distal end is withdrawn from at least a portion of the inner member distal end, and is elastically deformable operable to extend under the urging engagement of the tube member distal end when advanced over the inner member distal end.

In accordance with another embodiment, the tissue severing device further comprises a supporting means operable to support the inner member distal end in a curved position when the inner member distal end is at least partially exposed by the withdrawal of the tube member distal end.

In accordance with another embodiment, the supporting means comprises a fixed support ribbon. The fixed support ribbon comprises an elongated body including a fixed support ribbon proximal end and a fixed support ribbon distal end opposite the fixed support ribbon proximal end. The fixed support ribbon proximal end is coupled to the tube member distal end within the tube member lumen and the fixed support ribbon distal end is coupled to the inner member distal end. The tube member distal end is operable to advance over and receive the inner member distal end, the cutting element distal end, and the fixed support ribbon. The fixed support ribbon has a length that is operable to pull the inner member distal end into a curve with respect to the tube member axis when the tube member distal end is moved in a proximal direction and to substantially retain that curve when tissue is severed by the cutting element distal end.

In accordance with another embodiment, the inner member distal end is biased to a substantially straight orientation along the tube member axis. The fixed support ribbon is operable to provide a pulling force necessary to flex the inner member distal end into a curve as well as provide support to prevent the inner member distal end from significantly extending toward the tube member axis when the cutting element distal end is pulled through tissue to be severed.

In accordance with another embodiment, the tissue severing device further comprises a slidable support ribbon operable for supporting the inner member distal end in a curved position when the inner member distal end is at least partially exposed by the withdrawal of the tube member distal end. The slidable support ribbon comprises an elongated body including a slidable support ribbon proximal end and a slidable support ribbon distal end opposite the slidable support ribbon proximal end. The slidable support ribbon proximal end extends through the tube member lumen from about the tube member proximal end to about the tube member distal end and adjacent the inner member. The slidable support ribbon distal end is positioned adjacent the inner member distal end and the cutting element distal end.

In accordance with another embodiment, the tissue severing device further comprises an engagement ring coupled to the inner member distal end. The slidable support ribbon distal end and the inner member distal end are slidingly coupled by cooperative engagement of the inner member distal end and the engagement ring. The slidable support ribbon distal end comprises a substantially uniform width body portion and a flared portion at about the inner member distal end, wherein the flared portion has a width that is larger than the body portion. The engagement ring comprising a shape of a partial loop coupled to the inner member distal end transverse to an inner member axis. The engagement ring is operable to slidingly receive the body portion of the slidable support ribbon distal end and is undersized so as to not be able to receive the flared portion therethrough. The flared portion is operable as a catch such that there is no further axial movement of the slidable support ribbon distal end relative to the engagement ring when the flared portion engages the engagement ring. The engagement of the flare portion with the engagement ring is operable to provide a means for pulling the inner member distal end proximally and thus flex the inner member distal end to present the cutting element distal end to an angle to the tube member axis. The engagement ring is operable to be slidingly received within the tube member lumen.

In accordance with another embodiment, the cutting element comprises an elongated member that forms a contiguous element that defines a loop at the cutting element distal end and two ends at the cutting element proximal end.

In accordance with another embodiment, the cutting element distal end comprises a substantially elastic material such that the cutting element distal end comprises a diameter somewhat larger than the inner diameter of the tube member lumen. When the tube member distal end is advanced in the distal direction, the cutting element distal end substantially elastically deforms and is slidingly received within the tube member lumen and when the tube member distal end is advanced in the proximal direction, the cutting element distal end exits the tube member lumen and substantially elastically expands therefrom.

In accordance with another embodiment, the tissue severing device further comprises an energy source coupled to the cutting element and operable to assist the cutting element proximal end in cutting and severing tissue.

In accordance with another embodiment, the energy source is housed within the handle. The inner member further comprises at least one inner member lumen extending through the inner member proximal end and the inner member distal end. The cutting element comprises an elongated member that forms a contiguous element that defines a loop at the cutting element distal end and two ends at the cutting element proximal end. The cutting element proximal end extends through the inner member lumen to the handle and the two ends of the cutting element proximal end are coupled to the energy source.

In accordance with another embodiment, the tissue severing device further comprises an engagement means operable for moving the tube member proximally and distally over the inner member.

BRIEF DESCRIPTION OF THE DRAWINGS

Embodiments are illustrated by way of example and not by way of limitation in the figures of the accompanying drawings, in which like references may indicate similar elements throughout the various figures unless otherwise specified.

FIGS. 5A and 5B are side cut-away views of the device distal end showing an embodiment of a supporting means comprising a fixed support ribbon of an embodiment of the tissue severing device of FIG. 1B;

DETAILED DESCRIPTION

Figure 1A:
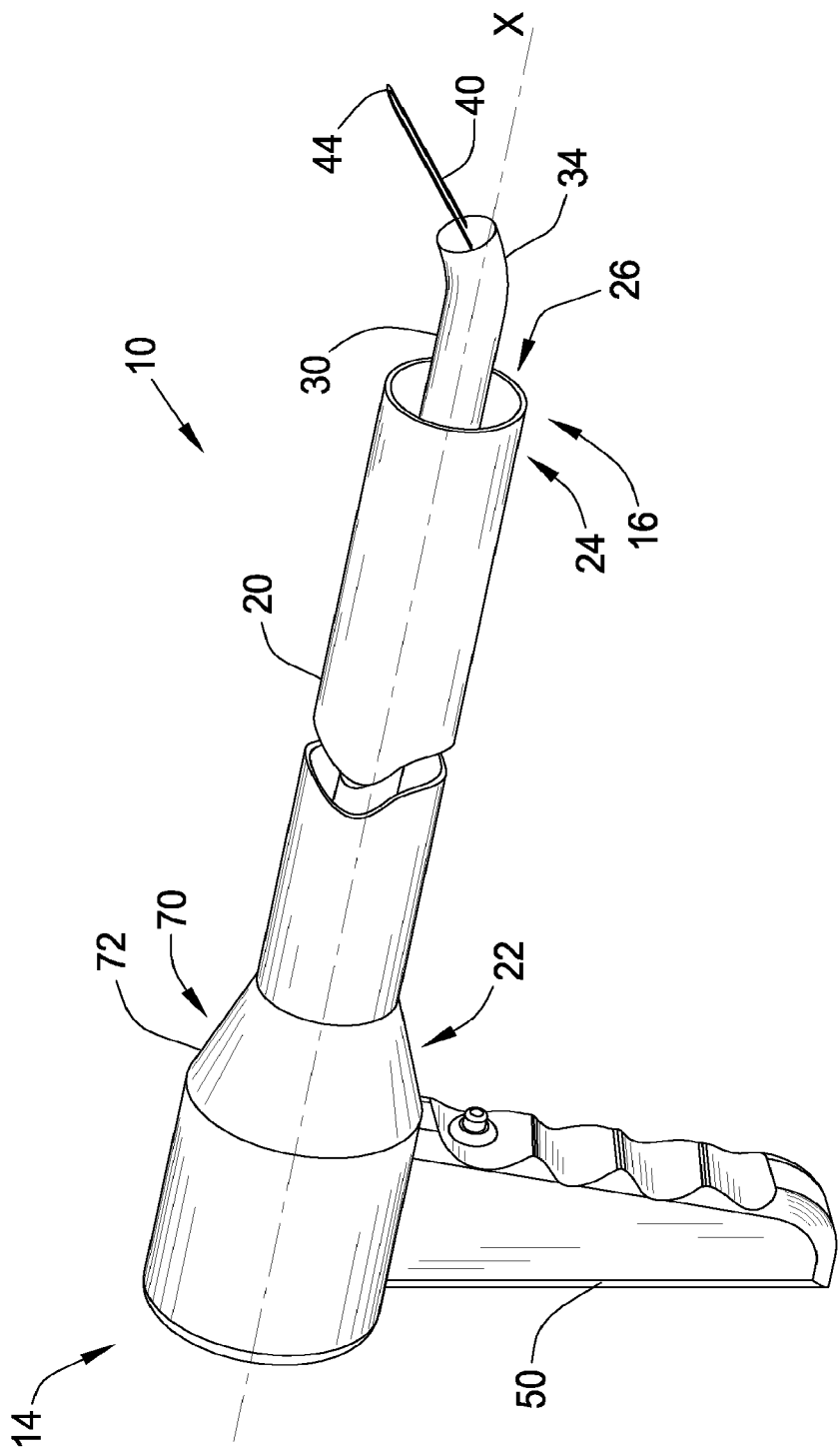
FIGS. 1A and 1B are perspective views of embodiments of tissue severing devices comprising a handle, a tube member, an inner member, and a cutting element.

In the following description, embodiments of apparatus and methods will be disclosed. For purposes of explanation, specific numbers, materials, and/or configurations are set forth in order to provide a thorough understanding of the embodiments. However, it will also be apparent to those skilled in the art that the embodiments may be practiced without one or more of the specific details, or with other approaches, materials, components, etc. In other instances, well-known structures, materials, and/or operations are not shown and/or described in detail to avoid obscuring the embodiments. Accordingly, in some instances, features are omitted and/or simplified in order to not obscure the disclosed embodiments. Furthermore, it is understood that the embodiments shown in the figures are illustrative representations and are not necessarily drawn to scale.

Reference throughout this specification to "one embodiment" or "an embodiment" means that a particular feature, structure, or characteristic described in connection with the embodiment is included in at least one embodiment of claimed subject matter. Thus, the appearances of the phrase "in one embodiment" or "an embodiment" in various places throughout this specification are not necessarily all referring to the same embodiment. Furthermore, the particular features, structures, or characteristics may be combined in one or more embodiments.

Reference will now be made to embodiments illustrated in the drawings and specific language which will be used to describe the same. It will nevertheless be understood that no limitation of the scope of the invention is thereby intended. Alterations and further modifications of the illustrated embodiments and further applications of the principles of the invention, as would normally occur to one skilled in the art to which the invention relates, are also within the scope of the invention.

Tissue severing devices as provided in embodiments herein are operable to be inserted through small surgical openings, such as, but not limited to, being inserted through a trocar sleeve at a laparoscopic port site and advanced to tissue to be severed or morcellated. The tissue severing device is operable to directly sever or morcellate tissue within a patient's body.

Figure 1B:
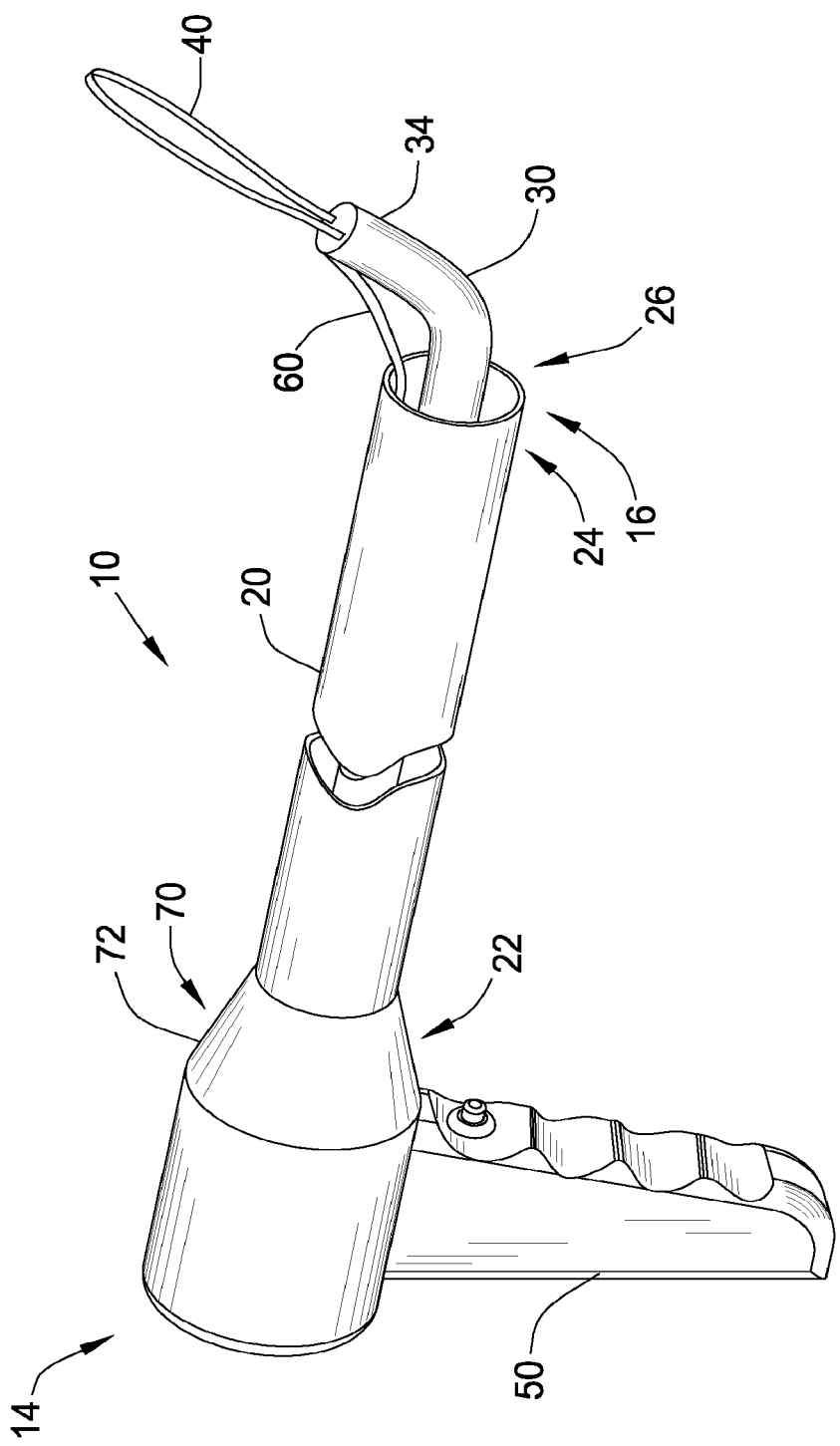

FIGS. 1A and 1B are perspective views of tissue severing devices 10 comprising a handle 50, a tube member 20, an inner member 30, and a cutting element 40, in accordance with two embodiments. The tube member 20 comprises an elongated relatively stiff tube having a tube member proximal end 22 extending into the handle 50 and a tube member distal end 24 opposite the tube member proximal end 22. The tube member 20 defines a tube member lumen 26 that extends through the tube member proximal end 22 to the tube member distal end 24 defining a tube member axis X. The inner member 30 comprises an elongated body having an inner member proximal end 32 (hidden from view) extending through the tube member lumen 26 and into the handle 50 and an inner member distal end 34 opposite the inner member proximal end 32. The inner member 30 is operable to be received within the tube member lumen 26.

Figure 18:
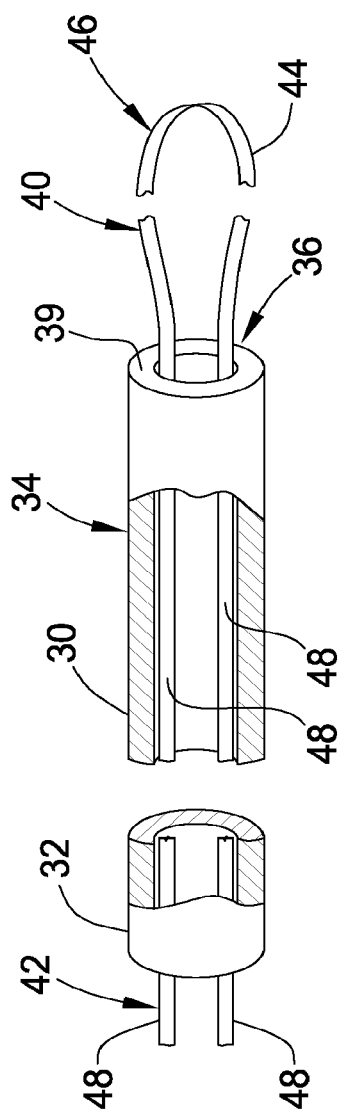
FIG. 18 is a partial cut-away view of an embodiment of a cutting element and an inner member, in accordance with an embodiment.

The cutting element 40 comprises a cutting element proximal end 42 (hidden from view) that enters the inner member distal end 34, shown in FIG. 18, and a cutting element distal end 44 opposite the cutting element proximal end 42. The cutting element distal end 44 extends from the inner member distal end 34.

The tissue severing device 10 includes a device proximal end 14 that generally includes the handle 50 and a device distal end 16 that generally includes the tube member distal end 24, the inner member distal end 34, and the cutting element distal end 44.

Figure 2A:
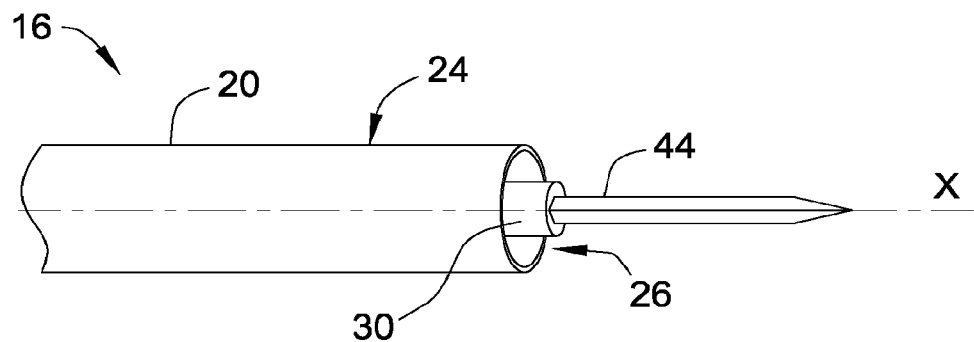
FIG. 2A is a side view of the device distal end showing the cutting element distal end extending from the tube member distal end of an embodiment of the tissue severing device of FIG. 1A.
Figure 2B:
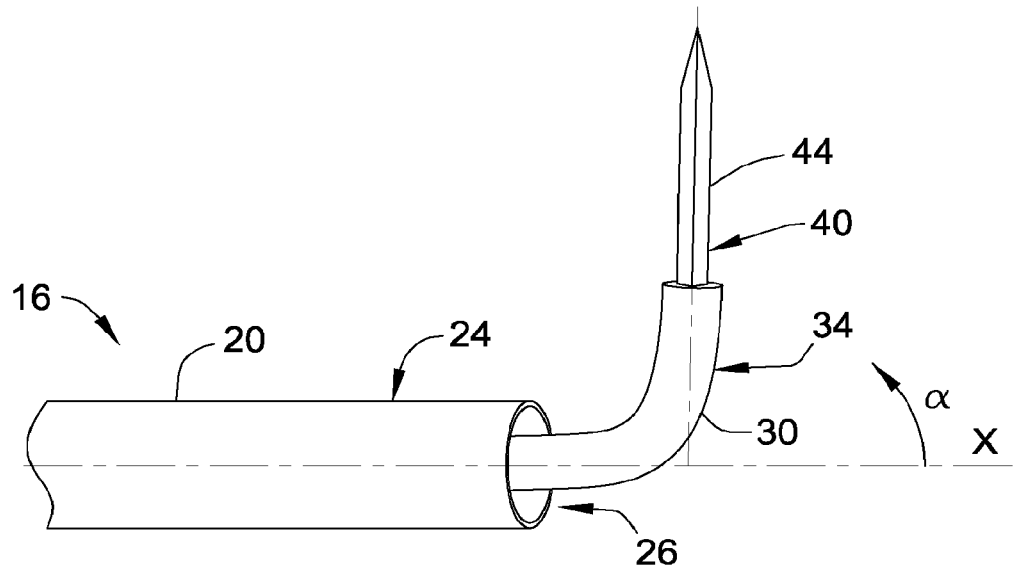
FIG. 2B is a side view of the device distal end showing the inner member distal end and the cutting element distal end extending from the tube member distal end of an embodiment of the tissue severing device of FIG. 1A.
Figure 3:
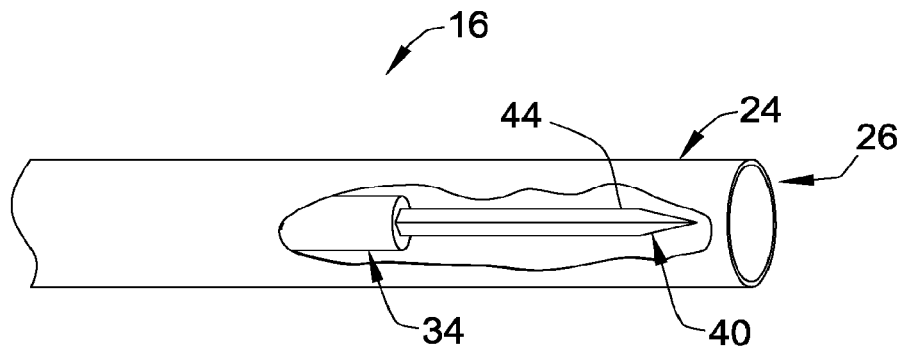
FIG. 3 is a side cut-away view of the device distal end showing the tube member distal end extending over and containing the inner member distal end and the cutting element distal end of an embodiment of the tissue severing device of FIG. 1A.

FIG. 2A is a side view of the device distal end 16 showing the cutting element distal end 44 extending from the tube member distal end 24. FIG. 2B is a side view of the device distal end 16 showing the inner member distal end 34 and the cutting element distal end 44 extending from the tube member distal end 24. FIG. 3 is a side cut-away view of the device distal end 16 showing the tube member distal end 24 extending over and containing the inner member distal end 34 and the cutting element distal end 44. The tube member distal end 24 is operable to move in a distal direction (away from the handle 50) over and with the tube lumen 26 operable to receive the inner member distal end 34 and the cutting element distal end 44 therein, as shown in FIG. 3. The tube member distal end 24 is also operable to move in a proximal direction (toward the handle 50) to expose the cutting element distal end 44, as shown in FIG. 2A, and, in other embodiments, also expose at least a portion of the inner member distal end 34, as shown in FIGS. 1A, 1B and 2B, so as to present the cutting element distal end 44 to tissue to be cut or severed.

Referring again to FIGS. 1A and 1B, in accordance with an embodiment, the tube member proximal end 22 includes an engagement means in cooperative engagement with the handle 50 operable to permit the tube member 20 to be moved proximally and distally over the inner member 30. It is anticipated that there are many engagement means that may be used to provide the function for permitting the movement of the tube member 20 proximally and distally over the inner member 30, some of which are described below.

The tube member 20 may comprise any suitable material, including, but not limited to, stainless steel, plastic, PTFE, polymer, and composite materials. In addition, the interior and/or exterior surfaces of the inner member 30 and tube member 20 may be coated with a low friction material such as, but not limited to, PTFE, Teflon®, polyvinylidene fluoride, polyethylene, or another polymeric material to facilitate movement of the tube member 20 with respect to the inner member 30 and cutting element distal end 44.

In accordance with an embodiment, the tissue severing device 10 is operable to present the cutting element distal end 44 extending from the tube member distal end 24 substantially parallel with the tube member axis X, as shown in FIG. 2A. The tube member distal end 24 is operable to move proximately such that the cutting element distal end 44 is exposed so as to be available for use to cut or sever tissue. In accordance with an embodiment, the inner member 30 may be relatively stiff so as to support the cutting element 40 from deflecting during use to cut or sever tissue.

Figure 4C:
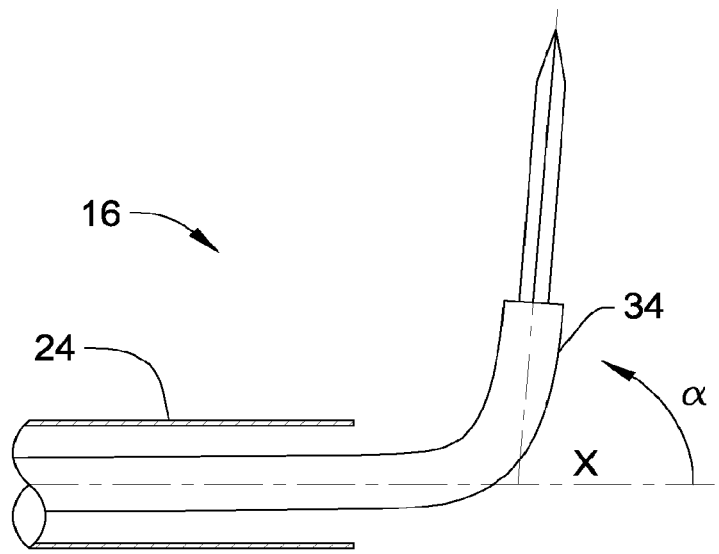
FIGS. 4A-4C are side views of the device distal end showing a progression of position of the inner member distal end in accordance with embodiment.
Figure 4B:
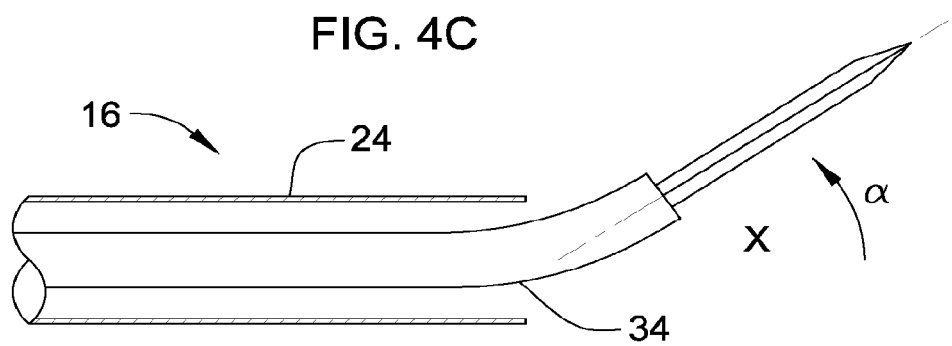
Figure 4A:
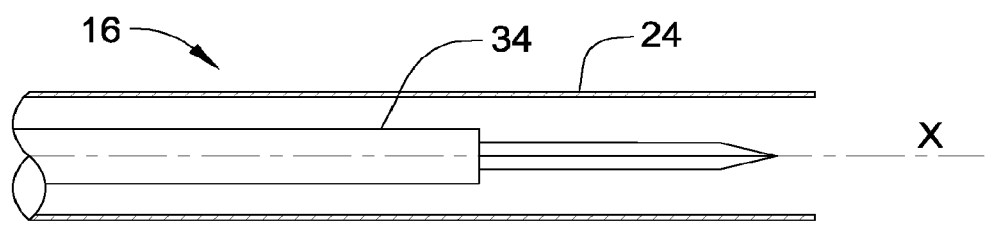

In accordance with another embodiment, the tissue severing device 10 is operable to present the cutting element distal end 44 at an angle alpha to the tube member axis X when the tube member distal end 24 is withdrawn from the cutting element distal end 44 and at least a portion of the inner member distal end 34, as shown in FIG. 2B. In accordance with an embodiment, the inner member distal end 34 is operable to curve away from and form an angle alpha with the tube member axis X when the inner member distal end 34 is exposed by the withdrawal of the tube member distal end 24 therefrom. FIGS. 4A-4C are side views of the device distal end 16 showing a progression of position of the inner member distal end 34. As the tube member distal end 24 withdraws from the inner member distal end 34, the angle alpha becomes progressively larger to a final predetermined angle alpha. In accordance with embodiments, the predetermined angle alpha may be any angle to the tube member axis X. In accordance with an embodiment, the predetermined angle alpha may be up to and including 90 degrees to the tube member axis X.

The tube member distal end 22, by being moved proximally or distally, may be used, among other things, to control the angle alpha of the cutting element distal end 44 and the cutting depth into the tissue as the tissue is being cut or severed.

In accordance with an embodiment, at least a portion of the inner member distal end 34 is biased to form a curve of a predetermined angle alpha when the tube member distal end 24 is withdrawn from over the inner member distal end 34. The means for providing the bias that affects the curve in the inner member distal end 34 may include one or a combination of the elastic properties of the tube member distal end 24 and a support means, as further described below.

In accordance with an embodiment, the at least a portion of the inner member distal end 34 that is elastically biased to form a curve of a predetermined angle alpha is elastically deformable so as to extend (straighten) under the urging engagement of the tube member distal end 24 advancing distally over the inner member distal end 34. The inner member distal end 34 and the cutting element distal end 44 are operatively stiff so as to prevent substantial extension or deflection of either or both of the inner member distal end 34 and the cutting element distal end 44 toward the tube member axis X under the forces encountered when the cutting element distal end 44 penetrates, cuts, and/or severs tissue, but not so stiff so as to prevent the extension of the inner member distal end 34 and the cutting element distal end 44 under the force of the tube member distal end 24 moving distally thereover.

In accordance with embodiments, the at least a portion of the inner member distal end 34 comprises any suitable material or assembly so as to be elastically deformable as well as either biased to be substantially straight or biased to form a curve of a predetermined angle alpha. Suitable materials include, but are not limited to, heat-set and cold-formed stainless steel and alloys thereof, super-elastic shape memory alloys including nickel-titanium alloys, preferentially-braided tubing and sleeves, and heat set or cold formed polymer and composite materials, among others, in forms such as, but not limited to, wires, ribbons, rods, sleeves, and tubes.

It is appreciated that there may be many apparatus that may be utilized to affect articulation of the inner member distal end 34. Such apparatus to affect articulation may include, but not limited to, one or more pivots, joints, extensible tubing, and rigid segments coupled by flexible or elastic interconnects. Embodiments representative of examples of such apparatus are provided in the discussion of FIGS. 25 and 26.

It is understood that the inner member 30 and the tube member 20 may comprise more than one material along the length of or at different portions of the inner member 30 and tube member 20 suitable for a particular purpose. By way of example, the inner member distal end 34 may be elastically deformable wherein the inner member proximal end 32 may be relatively stiffer as compared with the inner member distal end 34.

In accordance with other embodiments, and as an alternative to relying entirely on the elastic properties of the inner member distal end 34 to affect the suitable balance of stiffness for the particular purpose as described above, the tissue severing device 10 further comprises a support means. As also provided below, the support means may be used to the advantage of guiding tissue to be severed into the cutting element distal end 44 and controlling the depth of the cut, regardless of the support means' contribution to establishing the curve of the inner member distal end 34 or controlling extension of the inner member distal end 34 toward the tube member axis X while the cutting element distal end 44 is pulled through tissue to be severed.

In accordance with embodiments of the tissue severing device 10, the tissue severing device 10 further comprises supporting means for supporting the inner member distal end 34 in a curved position when the inner member distal end 34 is at least partially exposed by the withdrawal of the tube member distal end 24 therefrom. The supporting means may be used in combination with or in lieu of any bias to a predetermined curvature that may be present in the inner member distal end 34 as described above.

FIGS. 5A and 5B are side cut-away views of the device distal end 16 showing an embodiment of a supporting means comprising a fixed support ribbon 60, also shown in the embodiment of FIG. 1B. The fixed support ribbon 60 comprises an elongated body including a fixed support ribbon proximal end 62 and a fixed support ribbon distal end 64 opposite the fixed support ribbon proximal end 62. The fixed support ribbon proximal end 62 is coupled to the tube member distal end 24 within the tube member lumen 26 and the fixed support ribbon distal end 64 is coupled to the inner member distal end 34.

The tube member distal end 24 is operable to advance over and receive the inner member distal end 34, the cutting element distal end 44, and the fixed support ribbon 60, as shown in FIG. 5A. The tube member distal end 34 may be moved in the proximal direction so as to withdraw from the cutting element distal end 44, the inner member distal end 34, and a portion of the fixed support ribbon 60, as shown in FIG. 5B. The fixed support ribbon 60 has a length that is operable to pull the inner member distal end 34 into a curve and to substantially retain that curve as tissue is severed by the cutting element distal end 44.

Figure 6A:
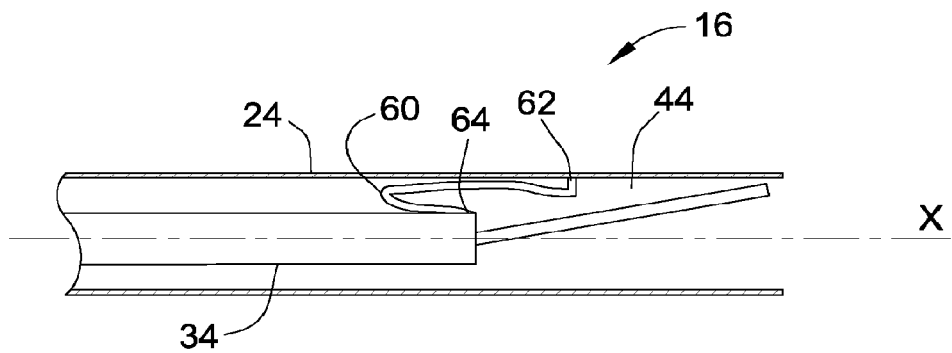
FIGS. 6A-6C are side views of the device distal end showing a progression of positions of the inner member distal end, in accordance with an embodiment.
Figure 6B:
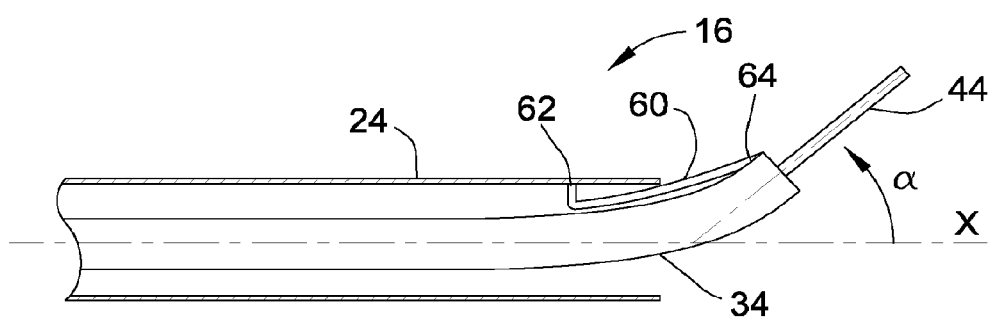
Figure 6C:
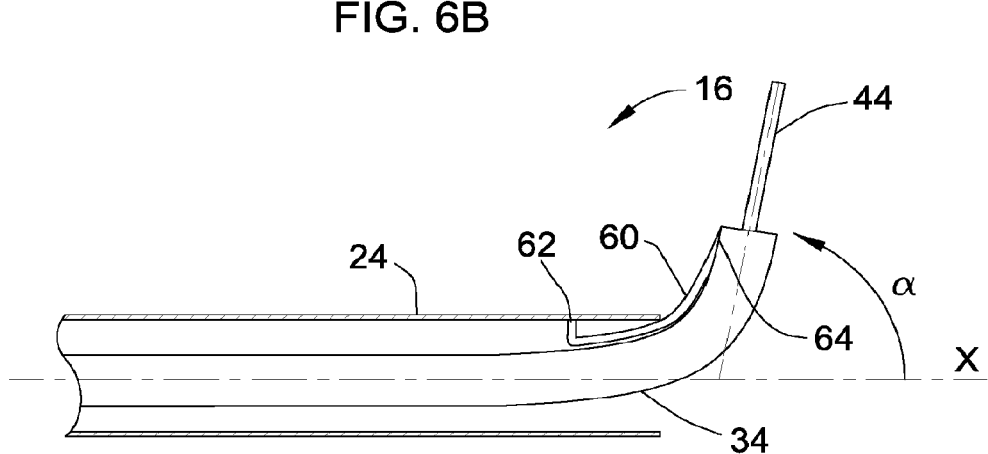

FIGS. 6A-4C are side views of the device distal end 16 showing a progression of positions of the inner member distal end 34. When the tube member distal end 24 covers the cutting element distal end 44, as shown in FIG. 6A, the fixed support ribbon 60 is generally slack and does not exhibit a significant force on the inner member distal end 34. As the tube member distal end 24 is moved proximally (toward the handle as shown in FIG. 1B), and moving the fixed support ribbon proximal end 62 proximally, exposing at least a portion of the inner member distal end 34, the fixed support ribbon 60 becomes taught and begins to exert a pulling force on the inner member distal end 34 which bends the inner member distal end 34 to an angle alpha to the tube member axis X dependent on the distance that the tube member distal end 24 has moved proximally, as shown in FIGS. 6B and 6C.

As the tube member distal end 24 is moved distally to progressively cover the inner member distal end 34, the fixed support ribbon proximal end 62 moves distally with the tube member distal end 24 allowing the inner member distal end 34 to extend toward the tube member axis X. In an embodiment wherein the inner member distal end 34 has a curve bias, that is, is biased to a predetermined curve, the fixed support ribbon 60 in combination with the tube member distal end 24 provides support to prevent the inner member distal end 34 from extending significantly toward the tube member axis X when the cutting element distal end 44 is pulled through tissue to be severed which may present forces that may overcome the curve bias of the inner member distal end 34 were it not for the fixed support ribbon 60. In addition, or in the alternative, the fixed support ribbon 60 assists in controlling the depth of cut of the cutting element distal end 44 by impinging on and guiding the tissue into the cutting element distal end 44, as will be discussed further below.

The fixed support ribbon 60 is operable to control the depth of cut into the tissue by the cutting element distal end 44. During use, the fixed support ribbon 60 slides along the tissue edge substantially preventing the cutting element distal end 44 from sinking into the tissue to a depth greater than the length of the cutting element distal end 44.

In an embodiment wherein the inner member distal end 34 has a straight bias, that is, is biased to a substantially straight orientation along the tube member axis X, the fixed support ribbon 60 in combination with the tube member distal end 24 provides the pulling force necessary to bend the inner member distal end 34 into a curve as well as provide support to prevent the inner member distal end 34 from significantly extending toward the tube member axis X when the cutting element distal end 44 is pulled through tissue to be severed. Additionally, the fixed support ribbon 60 assists in controlling the depth of cut of the cutting element distal end 44 by guiding the tissue to be severed into the cutting element distal end 44, as will be discussed further below.

The tube member distal end 24, by being moved proximally or distally, in combination with the fixed support ribbon 60, may be used, among other things, to control the angle alpha of the cutting element distal end 44 and the cutting depth into the tissue as the tissue is being cut or severed.

Figure 7A:
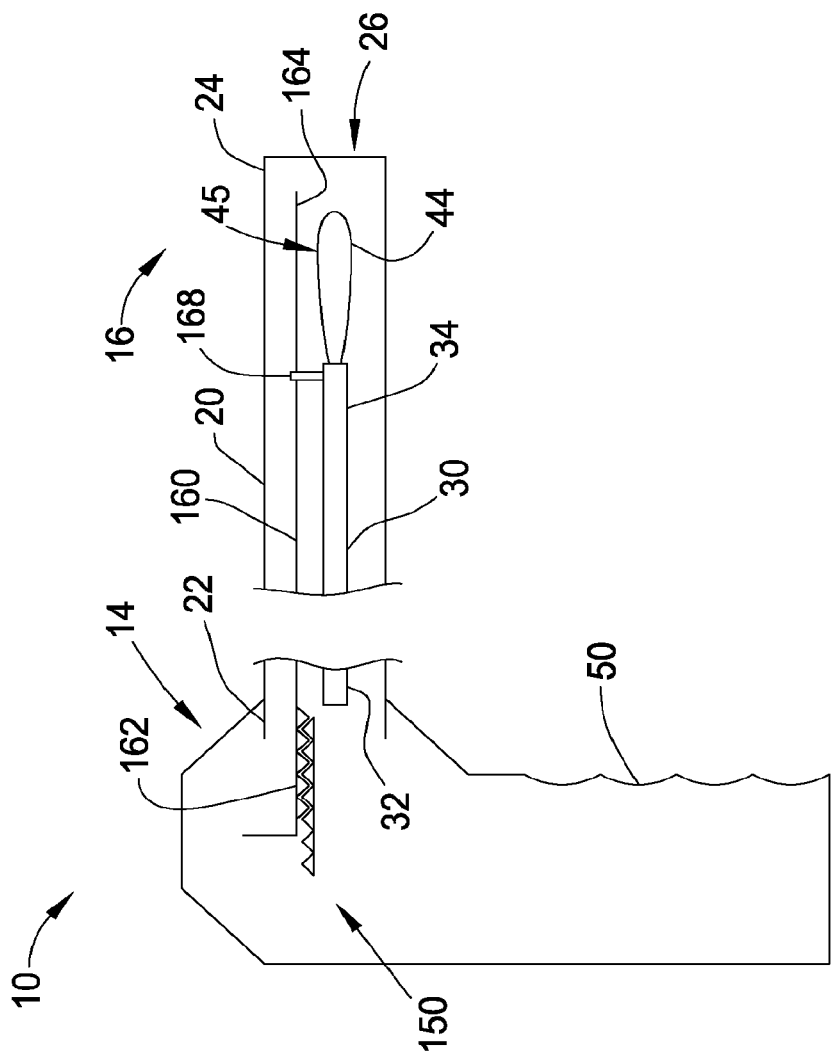
FIG. 7A is a side, partial cut-away view of a tissue severing device 10 in accordance with an embodiment.
Figure 7B:
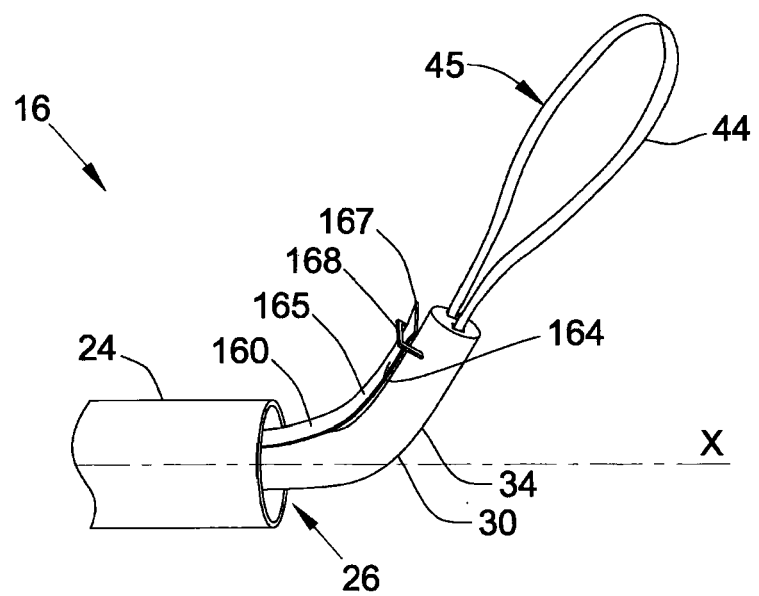
FIGS. 7B-7C are perspective and top views, respectively, of the device distal end showing a slidable support ribbon as another embodiment of a supporting means operable for supporting the inner member distal end in a curved position when the inner member distal end is at least partially exposed by the withdrawal of the tube member distal end.
Figure 7C:
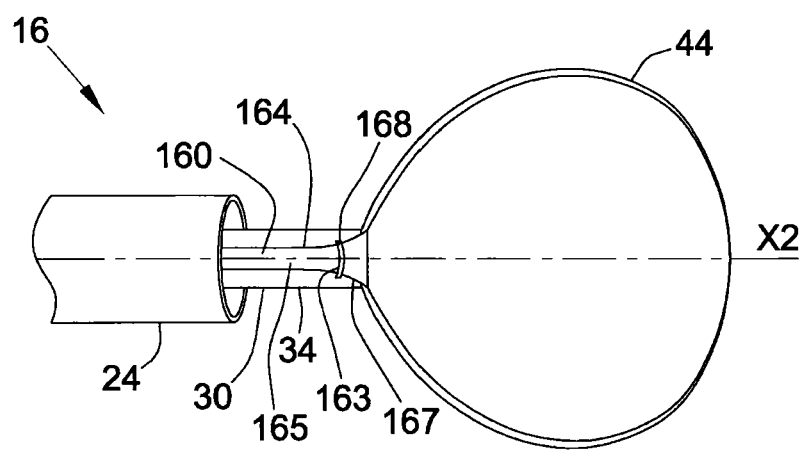

FIG. 7A is a side, partial cut-away view of a tissue severing device 10 and FIGS. 7B-7C are perspective and top views, respectively, of the device distal end 16 showing a slidable support ribbon 160 as another embodiment of a supporting means operable for supporting the inner member distal end 34 in a curved position when the inner member distal end 34 is at least partially exposed by the withdrawal of the tube member distal end 24. The slidable support ribbon 160 may be used in combination with or in lieu of any bias to a predetermined curvature that may be present in the inner member distal end 34.

The slidable support ribbon 160 comprises an elongated body including a slidable support ribbon proximal end 162 and a slidable support ribbon distal end 164 opposite the slidable support ribbon proximal end 162. The slidable support ribbon proximal end 162 extends through the tube member lumen 26 from about the tube member proximal end 22 to the tube member distal end 24 and adjacent the inner member 30. The slidable support ribbon distal end 164 is positioned adjacent the inner member distal end 34 and the cutting element distal end 44 and is operably engaged therewith as detailed below.

The slidable support ribbon proximal end 162 is positioned generally adjacent the handle 50 and may be operably engaged by the user or elements of the tissue severing device 10 as detailed below.

In accordance with an embodiment, the slidable support ribbon distal end 164 is operable to support the inner member distal end 34 into a curved shape when the tube member distal end 24 is withdrawn therefrom. The slidable support ribbon 160 is operable to substantially prevent the inner member distal end 34 from extending toward the tube member axis X when the cutting element distal end 44 is pulled through tissue to be severed. The slidable support ribbon 160 is also operable to, among other things, control the depth of cut into the tissue by guiding the tissue toward the cutting element distal end 44.

In another embodiment, the slidable support ribbon distal end 164 is also operable to, among other things, protect the tube member lumen 26 from being damaged by a sharp edge 45 of the cutting element distal end 44 by acting as a barrier therebetween. In accordance with an embodiment, the slidable support ribbon distal end 164 comprises a relatively flat profile so as to cover at least a portion of the cutting element distal end 44 when the slidable support ribbon distal end 164 is extended there over. The slidable support ribbon distal end 164 is operable to extend between a sharp edge 45, shown in FIG. 7C, of the cutting element distal end 44 and a portion of the tube member lumen 26 when the tube member distal end 24 is extended over the cutting element distal end 44. The slidable support ribbon distal end 164 is operable to withdraw from adjacent the sharp edge 45 of the cutting element distal end 44 when the tube member distal end 24 is withdrawn from over the cutting element distal end 44.

In accordance with an embodiment, the slidable support ribbon distal end 164 is operable to begin withdrawing proximally from being adjacent the cutting element distal end 44 as the cutting element distal end 44 begins to be exposed by the withdrawing tube member distal end 24. In this embodiment, the slidable support ribbon distal end 164 is exposed substantially concurrently with the exposure of the inner member distal end 34 by the tube member distal end 24. In other words, the slidable support ribbon distal end 164 is not adjacent the portion of the cutting element distal end 44 that is exposed by the withdrawing tube member distal end 24 such that the cutting element distal end 44 may begin severing tissue immediately upon withdrawal of the tube member distal end 24.

In accordance with another embodiment, the slidable support ribbon distal end 164 is operable to at least partially be adjacent the cutting element distal end 44 as the cutting element distal end 44 and the slidable support ribbon distal end 164 are exposed by the withdrawing tube member distal end 24. In this embodiment, the slidable support ribbon distal end 164 is withdrawn from adjacent the cutting element distal end 44 after the cutting element distal end 44 is at least substantially exposed by the withdrawing tube member distal end 24. The slidable support ribbon distal end 164 may come between at least a portion of the sharp edge 45 of the cutting element distal end 44 and adjacent tissue near which it is placed. The user may withdraw the slidable support ribbon distal end 164 into the tube member lumen 26 in which the cutting element distal end 44 may then sever tissue.

In another embodiment, as the tube member distal end 24 is further withdrawn so as to expose a portion of the inner member distal end 34, the slidable support ribbon distal end 164 is withdrawn from adjacent the cutting element distal end 44 and operably engages the inner member distal end 34 so as to provide at least one of the following functions, including, but not limited to, support the inner member distal end 34 into an arc shape, to substantially prevent the inner member distal end 34 from extending toward the tube member axis X while the cutting element distal end 44 is pulled through tissue to be severed, and control the depth of cut into the tissue by guiding the tissue toward the cutting element distal end 44.

The slidable support ribbon 160 is operable to control the depth of cut into the tissue by the cutting element distal end 44. During use, the slidable support ribbon 160 slides along the tissue edge substantially preventing the cutting element distal end 44 from sinking into the tissue to a depth greater than the length of the cutting element distal end 44.

As discussed above, the slidable support ribbon distal end 164 and the tube member distal end 24 are operably engaged to provide the desired functions. In accordance with the embodiments of FIGS. 7A-7C, the slidable support ribbon distal end 164 is slidingly coupled to the inner member distal end 34. As the inner member distal end 34 is exposed by the withdrawing tube member distal end 24, the user may pull the slidable support ribbon proximal end 162 in the proximal direction so as to withdraw the slidable support ribbon proximal end 162 from adjacent the cutting element distal end 44 and bend the inner member distal end 34 into a desired arc to present the cutting element distal end 44 to the tissue at an angle alpha to the tube member axis X. The user may control the slidable support ribbon proximal end 162 in a desired position by pulling or pushing the slidable support ribbon proximal end 162.

In accordance with an embodiment, the slidable support ribbon distal end 164 and the inner member distal end 34 are slidingly coupled by cooperative engagement of the inner member distal end 34 and an engagement ring 168 coupled to the inner member distal end 34. The slidable support ribbon distal end 164 comprises a substantially uniform width body portion 165 and a flared portion 167 at the slidable support ribbon distal end 164, wherein the flared portion 167 has a width that is larger than the body portion 165.

The engagement ring 168 comprises a shape of a partial loop and is coupled to the inner member distal end 34 transverse to an inner member axis X2. The engagement ring 168 is operable to slidingly receive the body portion 165 of the slidable support ribbon distal end 164 but is undersized so as to not be able to receive the flared portion 167 therethrough. The flared portion 167, thus, functions as a catch such that there is no further axial movement of the slidable support ribbon distal end 164 relative to the engagement ring 168 when the flared portion 167 engages the engagement ring 168. Therefore, the engagement of the flare portion 167 with the engagement ring 168 provides a means for pulling the inner member distal end 34 proximally and thus flex the inner member distal end 34 into a desired arc to present the cutting element distal end 44 at an angle alpha to the tube member axis X.

Figure 7D:
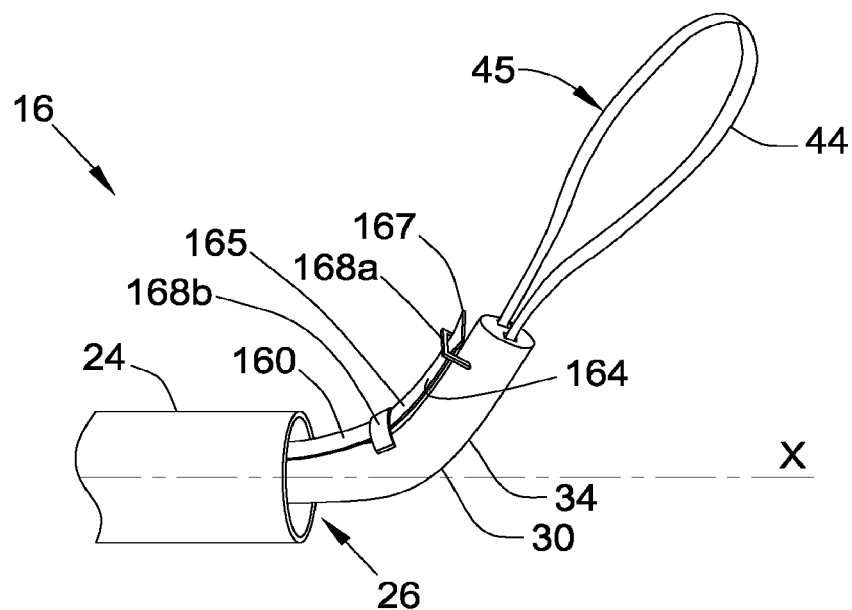
FIG. 7D is a perspective view of a device distal end comprising a slidable support ribbon and a plurality of engagement rings, in accordance with another embodiment.

FIG. 7D is a perspective view of the device distal end 16 comprising a slidable support ribbon 160 and a plurality of engagement rings 168a, 168b in accordance with another embodiment. The plurality of engagement rings 168a, 168b are operable to support the slidable support ribbon 160 in conformance with the curved position of the inner member distal end 34 when the inner member distal end 34 is at least partially exposed by the withdrawal of the tube member distal end 24.

Figure 8:
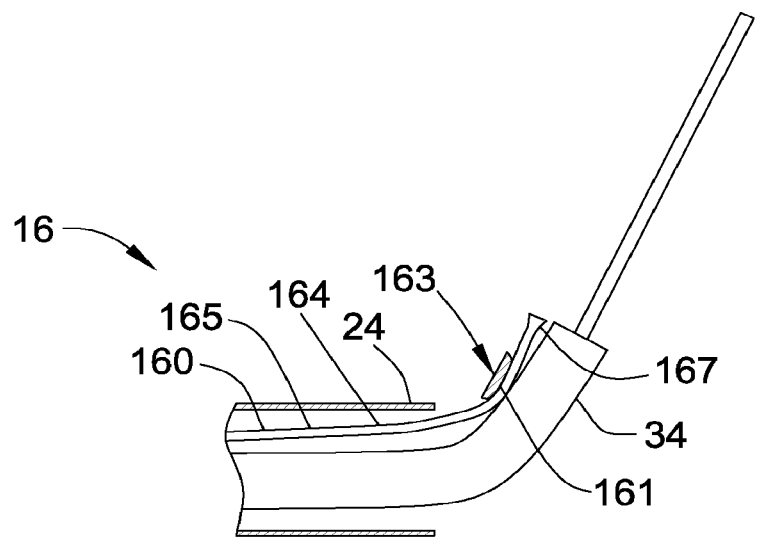
FIG. 8 is a cross-sectional view of the inner member distal end, a portion of the body portion of the slidable support ribbon distal end, and an engagement ring, in accordance with an embodiment.

The engagement ring 168 is operable to be slidingly received within the tube member lumen 26. FIG. 8 is a cross-sectional view of the inner member distal end 34, a portion of the body portion 165 of the slidable support ribbon distal end 164, and an embodiment of the engagement ring 168. To assist in guiding the tube member distal end 24 over the engagement ring 168 so as to contain the engagement ring 168, the engagement ring 168 comprises a proximal edge 163 that is sloped facing proximally so as to guide the tube member distal end 24 over the engagement ring 168.

The engagement ring 168 is operable to slidingly receive the body portion 165 of the slidable support ribbon distal end 164. In accordance with an embodiment, the engagement ring 168 comprises an inner surface 161 that has a convex shape facing distally so as to assist in guiding the body portion 165 of the slidable support ribbon distal end 164 between the engagement ring 168 and the inner member distal end 34. This may be particularly advantageous when the slidable support ribbon distal end 164 is caused to flex at an angle so as to pull and/or support the inner member distal end 34 at an angle to the tube member axis X.

In accordance with an embodiment, the pullback of the slidable support ribbon 160 in the proximal direction so as to bend the inner member distal end 34 into a desired curve to present the cutting element distal end 44 at an angle alpha to the tube member axis X, and visa versa, may be done in a manual operation by the user or an automatic operation by the tissue cutting device 10. In accordance with an embodiment wherein the slidable support ribbon 160 is manually controlled, the slidable support ribbon proximal end 162 is operable to be manipulated by the user. In accordance with an embodiment, as shown in FIG. 7A, the slidable support ribbon proximal end 162 extends from the handle 50 such that the slidable support ribbon proximal end 162 may be grasped by the user. The slidable support ribbon proximal end 162 and the handle 50 may also comprise an engagement element such that the slidable support ribbon proximal end 162 may be releasably coupled to the handle 50 when the slidable support ribbon 160 is extended or retracted to a desired position. The engagement element allows for temporarily fixating the position of the slidable support ribbon proximal end 162.

It is anticipated that there are many suitable engagement elements that provide the function for releasably coupling the slidable support ribbon proximal end 162 to the handle 50. In an embodiment of an engagement element, by way of example only and not limited thereto, as shown in FIG. 7A, a ratchet 150 may be operably engaged between the slidable support ribbon proximal end 162 and the handle 50. The ratchet 150 allows for motion in the proximal direction while preventing motion in the distal direction until controlled release. As is known in the art, a ratchet 150 may comprise many devices, such as, but not limited to, a pair of racks with intermeshing teeth, and a toothed gear and pawl.

It is appreciated that the movement of the slidable support ribbon 160 may also be controlled by an electrical device, such as, but not limited to, an electric motor. In accordance with an embodiment, the slidable support ribbon proximal end 162 is engaged with a motor that is automatically or manually controlled operable to move the slidable support ribbon 160 proximally and distally.

In accordance with an embodiment wherein the slidable support ribbon 160 is automatically controlled by the tissue severing device 10, the slidable support ribbon proximal end 162 is operable to be manipulated by an interaction of elements of the tissue severing device 10.

In accordance with an embodiment wherein the slidable support ribbon 160 is automatically controlled, the slidable support ribbon proximal end 162 is cooperatively engaged with the tube member proximal end 22 such that when the tube member proximal end 22 is moved axially, the slidable support ribbon 160 may be moved axially as well. It is anticipated that there are many apparatus that may affect cooperation between the slidable support ribbon proximal end 162 and the tube member proximal end 22.

FIGS. 9A-9D are side views of an embodiment of a mechanism for controlling the movement of the slidable support ribbon 160 under the influence of the movement of the tube member 20. The slidable support ribbon proximal end 162 further comprises a snare 166 extending at an angle from the slidable support ribbon proximal end 162 operable to catch a tube member proximal edge 21 of the tube member proximal end 22.

Figure 9A:
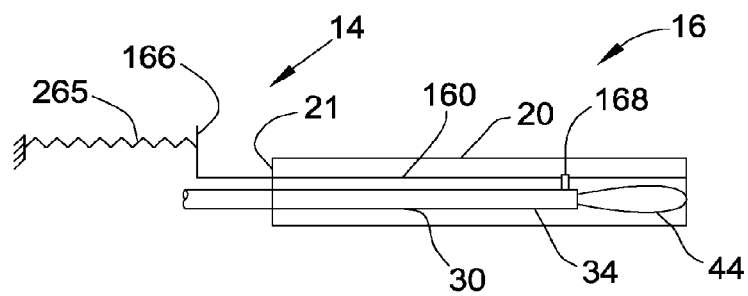
FIGS. 9A-9D are side views of an embodiment of a mechanism for controlling the movement of the slidable support ribbon under the influence of the movement of the tube member.
Figure 9B:
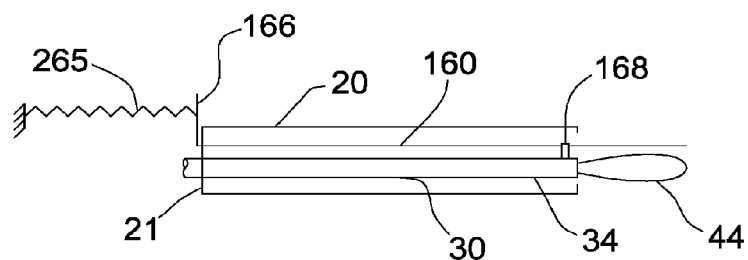
Figure 9C:
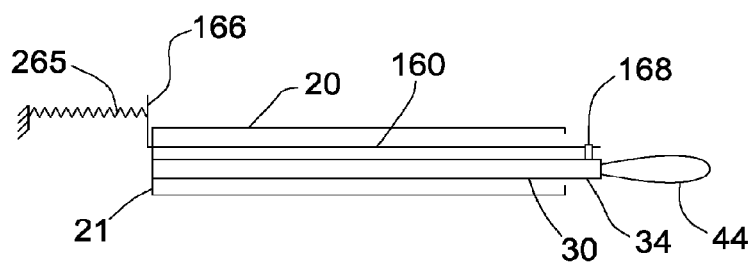
Figure 9D:
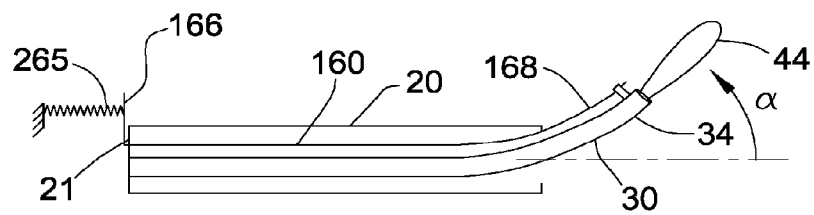

FIG. 9A shows a simplified view of the tube member 20 in the distal position wherein the cutting element 40 is contained within the tube member lumen 26. The snare 166 is spaced a predetermined distance from the tube member proximal edge 21. The predetermined distance may be substantially the same as the length of the cutting element 40 such that when the tube member distal end 24 has retracted from the cutting element distal end 44, the tube member proximal edge 21 may engage the snare 166, as shown in FIG. 9B. As the tube member 20 is moved further in the proximal direction, the tube member proximal edge 21 engages the snare 166 so as to pull the slidable support ribbon 160 in the proximal direction and thus move the slidable support ribbon distal end 164 from adjacent the cutting element distal end 44, as shown in FIG. 9C. As the tube member 20 is moved further in the proximal direction, the slidable support ribbon 160 is moved further in the proximal direction and thus the slidable support ribbon distal end 164 engages the inner member distal end 34 so as to support the cutting element distal end 44 at an angle alpha to the tube member axis X. In accordance with an embodiment, the slidable support ribbon distal end 164 may be coupled to a biasing element 265 such that the slidable support ribbon 160 is urged to move in the distal direction when the tube member 20 is moved in the distal direction.

Figure 10A:
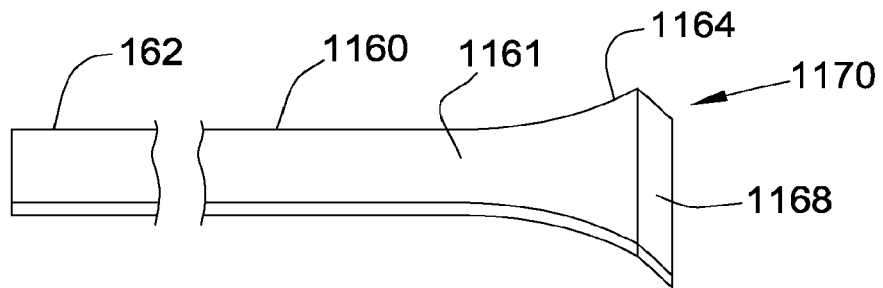
FIGS. 10A and 10B are perspective and side views, respectively, of a distal end of another embodiment of a slidable support ribbon.
Figure 10B:
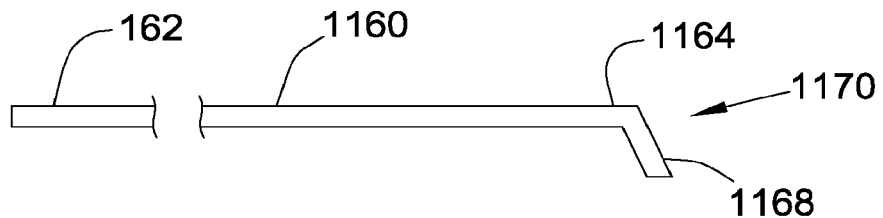

FIGS. 10A and 10B are perspective and side views, respectively, of a distal end 1164 of another embodiment of a slidable support ribbon 1160. The slidable support ribbon 1160 is an embodiment of a supporting means that is operable for supporting the inner member distal end 34 in a curved position when the inner member distal end 34 is at least partially exposed by the withdrawal of the tube member distal end 24 and operable to support the cutting element distal end 44 in an open position. The slidable support ribbon 1160 may be used in combination with or in lieu of any bias to a predetermined curvature, including straight, that may be present in the inner member distal end 34.

Figure 11A:
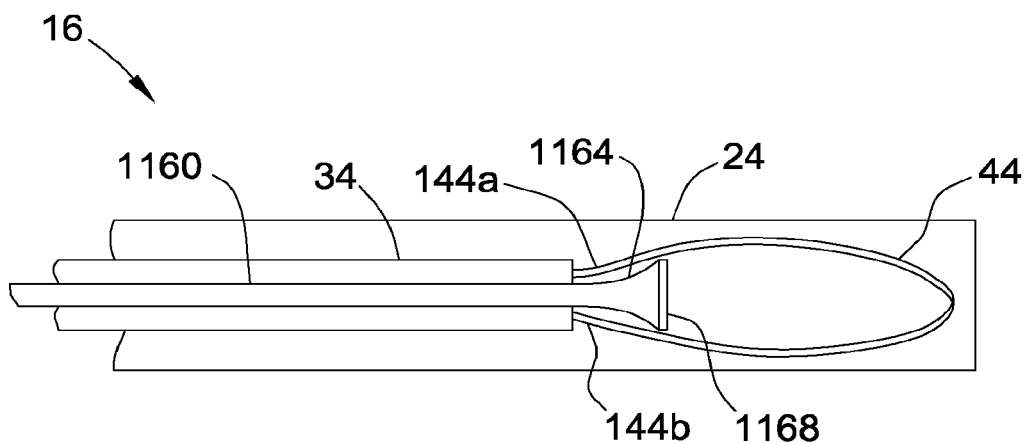
FIGS. 11A-11C are top, perspective, and top views, respectively, of the device distal end with the slidable support ribbon, in accordance with an embodiment.
Figure 11B:
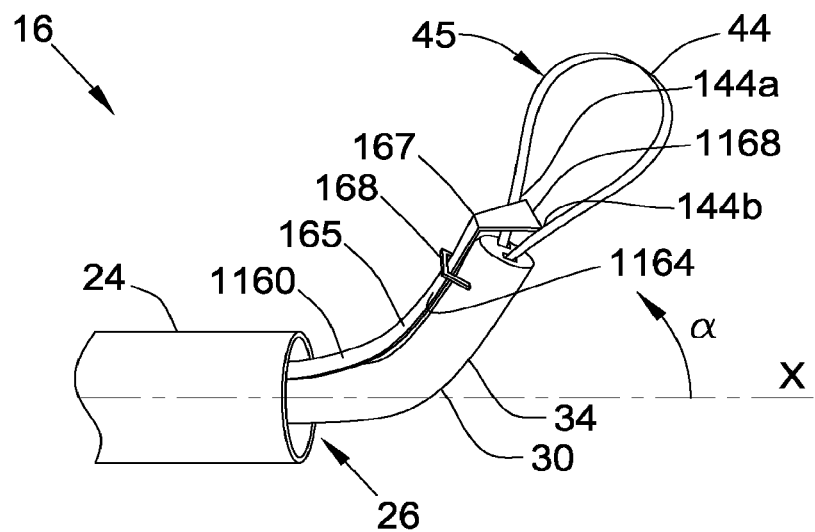
Figure 11C:
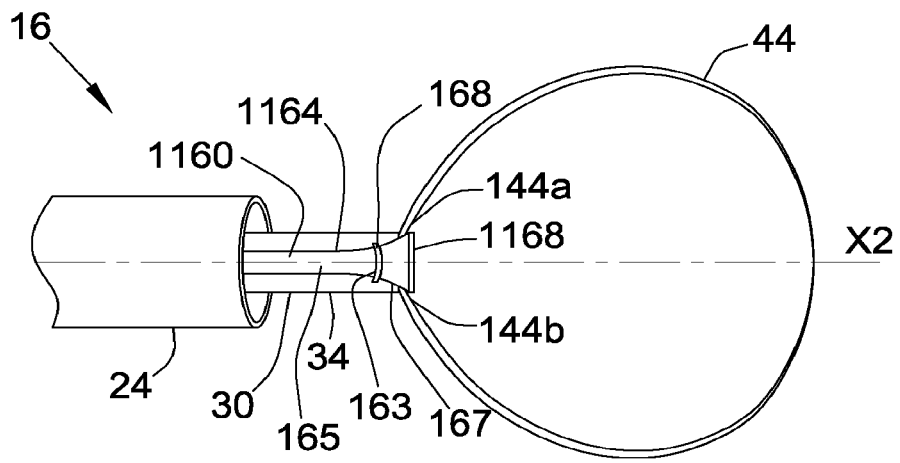

The slidable support ribbon 1160 comprises an elongated body including a slidable support ribbon proximal end 162, a slidable support ribbon distal end 1164 opposite the slidable support ribbon proximal end 162, and a ribbon body portion 1161 therebetween. The slidable support ribbon distal end 1164 comprises a cutting element engagement element 1170 operable to engage the cutting element portions 144*a*, 144*b* of the cutting element distal end 44 about the inner member distal end 34 as shown in FIGS. 11B-11C and discussed below. In accordance with the embodiment of FIGS. 10A-10B, the cutting element engagement element 1170 comprises a flange 1168 depending at about a 90 degree angle from the ribbon body portion 1161. The flange 1168 is operable to be received within the loop formed by the cutting element distal end 44.

Substantially similar to the embodiment of the slidable support ribbon 160 of FIG. 7A, the slidable support ribbon proximal end 162 of the slidable support ribbon 1160 extends through the tube member lumen 26 from about the tube member proximal end 22 to the tube member distal end 24 and adjacent the inner member 30. FIGS. 11A-11C are top, perspective, and top views, respectively, of the device distal end 16 with the slidable support ribbon 1160 in accordance with an embodiment. The slidable support ribbon distal end 1164 is positioned adjacent the inner member distal end 34 and the cutting element distal end 44 and is operably engaged therewith as detailed below.

As shown in FIG. 11A, when the cutting element distal end 44 is positioned within the tube member distal end 24, the flange 1168 of the slidable support ribbon distal end 1164 is positioned within the loop formed by the cutting element distal end 44 and does not substantially engage the cutting element distal end 44. As shown in FIGS. 11B-11C, when the cutting element distal end 44 is exposed by the withdrawal of the tube member distal end 24, the slidable support ribbon 1160 may be moved proximally such that the flange 1168 engages the cutting element portions 144*a*, 144*b* of the cutting element distal end 44 assisting in spreading apart the cutting element portions 144*a*, 144*b* and thus assisting in opening and stabilizing the loop formed by the cutting element distal end 44. The flange 1168 helps to stabilize, or hold-open, the cutting element distal end 44 during subsequent tissue severing. The flared portion 167 of the slidable support ribbon distal end 1164 engages the engagement ring 168 reducing any further traction on the cutting element distal end 44 by the flange 1168.

The slidable support ribbon distal end 1164 is also operable to support the inner member distal end 34 into a curved shape at an angle alpha to the tube member axis X when the tube member distal end 24 is withdrawn therefrom. The slidable support ribbon 1160 is operable to substantially prevent the inner member distal end 34 from extending toward the tube member axis X when the cutting element distal end 44 is pulled through tissue to be severed. The slidable support ribbon 1160 is also operable to, among other things, control the depth of cut into the tissue by guiding the tissue toward the cutting element distal end 44.

Substantially similar to the embodiment of FIG. 7A, the slidable support ribbon distal end 1164 is slidingly coupled to the inner member distal end 34 by an engagement ring 168. The slidable engagement of the slidable support ribbon 1160 of FIGS. 11A-11C is substantially the same as the slidable engagement of the embodiments of FIGS. 7A-7C. In accordance with an embodiment, the slidable support ribbon distal end 1164 is flared so as to engage the engagement ring 168 so as to position the cutting element distal end 44 as described above and shown in FIG. 11B. The slidable support ribbon distal end 1164 is flared also so as to provide a broader flange 1168 so as to more greatly engage and spread apart the cutting element portions 144a, 144b of the cutting element distal end 44.

Figure 12:
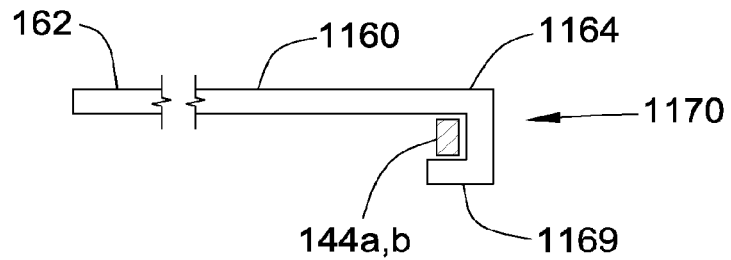
FIG. 12 is a side view of a cutting element engagement element comprising a U-shaped flange, in accordance with an embodiment.

It is appreciated that the cutting element engagement element 1170 of the slidable support ribbon distal end 1164 that is operable to engage the cutting element portions 144a, 144b of the cutting element distal end 44 may have a shape suitable for a particular purpose. FIG. 12 is a side view of a cutting element engagement element 1170 comprising a U-shaped flange 1169 operable to engage and substantially wrap around the cutting element portions 144a, 144b of the cutting element distal end 44. The U-shaped flange 1169 is operable to contain a portion of the cutting element portions 144a, 144b therein so as to prevent the cutting element portions 144a, 144b from slipping from the engagement of the U-shaped flange 1169.

It is appreciated that direct contact of the cutting element engagement element 1170 with the cutting element portions 144a, 144b may not be suitable for every purpose. By way of example, but not limited thereto, direct contact may reduce freedom of movement of the cutting element distal end 44 when energized by an energy source as discussed below. By way of another example, but not limited thereto, direct contact may cause electrical conductivity issues when the cutting element distal end 44 is energized by an electrical source such as in electrocautery. It is appreciated that there are many ways to prevent the direct contact between the cutting element engagement element 1170 and the cutting element portions 144a, 144b themselves when the cutting element engagement element 1170 is moved proximally so as to assist in spreading apart the cutting element portions 144a, 144b and thus opening or making more circular the loop formed by the cutting element distal end 44.

Figure 13:
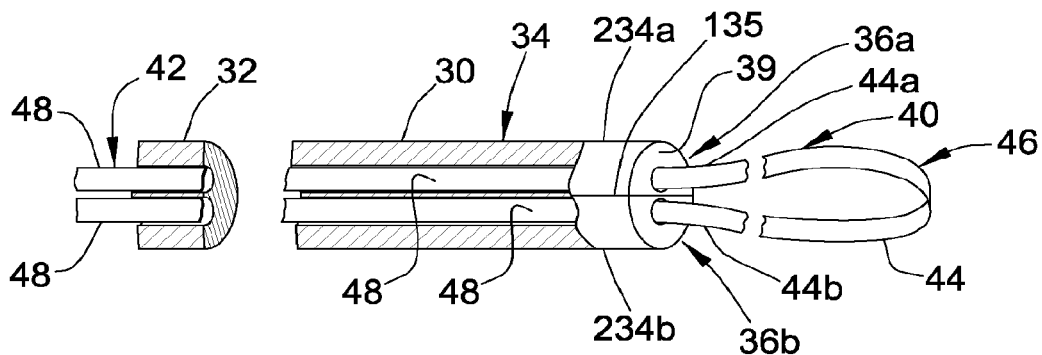
FIG. 13 is a side, partial cut-away view of an inner member, in accordance with an embodiment.

FIG. 13 is a side, partial cut-away view of an inner member 30 further comprising two inner member lumens 36a,b that are substantially parallel and that extend from the inner member proximal end 32 to the inner member distal end 34 therethrough, in accordance with an embodiment. The inner member distal end 34 further comprises a slit 135 between the two inner member lumens 36a,b, that extends from the inner member distal end 34 to a predetermined distance proximally operable to produce a bifurcation of the inner member distal end 34 defining two branch portions 234a,b each containing one of the two inner member lumens 36a,b. The two inner member lumens 36a,b are operable such that each of the cutting element portions 144a, 144b of the cutting element distal end 44 may be received and extend into one of the two inner member lumens 36a,b.

Figure 14:
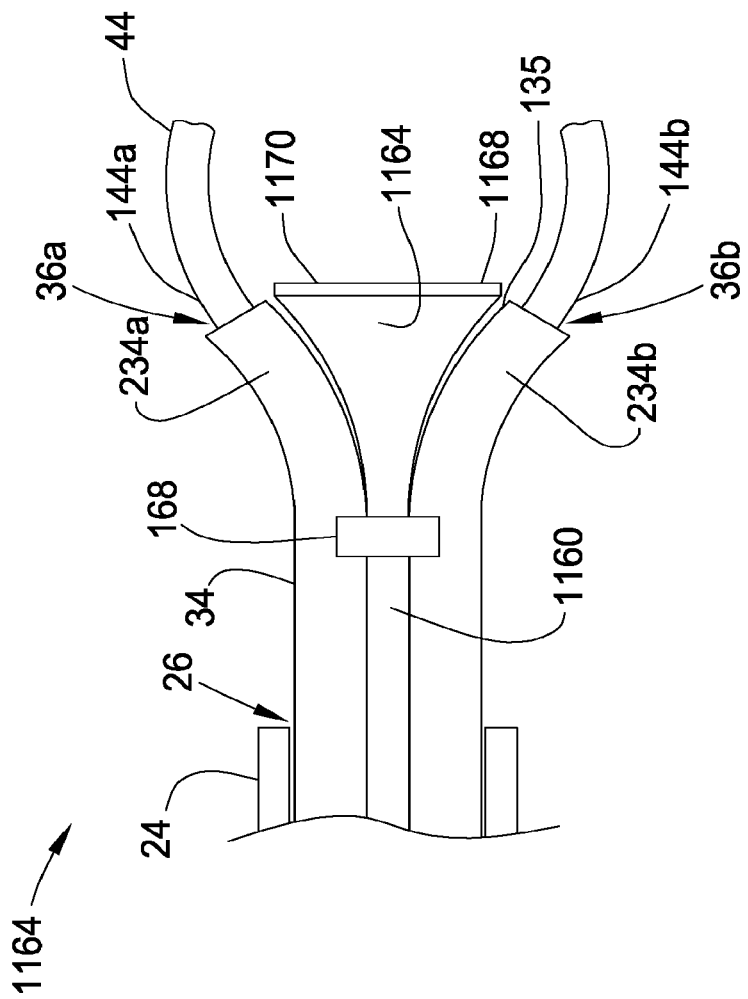
FIG. 14 is a top view of the device distal end showing a bifurcated inner member distal end, in accordance with the embodiment of FIG. 13.

FIG. 14 is a top view of the device distal end 16 showing a bifurcated inner member distal end 34 in accordance with the embodiment of FIG. 13. The inner member distal end 34 is bifurcated along the slit 135, the bifurcation being formed under the urging engagement of one or more of the spring bias of the cutting element 44 and the cutting element engagement element 1170 of the slidable support ribbon distal end 1164. In the case of the cutting element engagement element 1170, the cutting element engagement element 1170 engages the two branch portions 234a,b of the inner member distal end 34 about the cutting element portions 144a, 144b of the cutting element distal end 44 effectively creating and/or supporting the bifurcation of the inner member distal end 34. The cutting element engagement element 1170 engages the two branch portions 234a,b as shown in FIG. 14 rather than the cutting element portions 144a, 144b themselves as shown in FIG. 11B.

Figure 15:
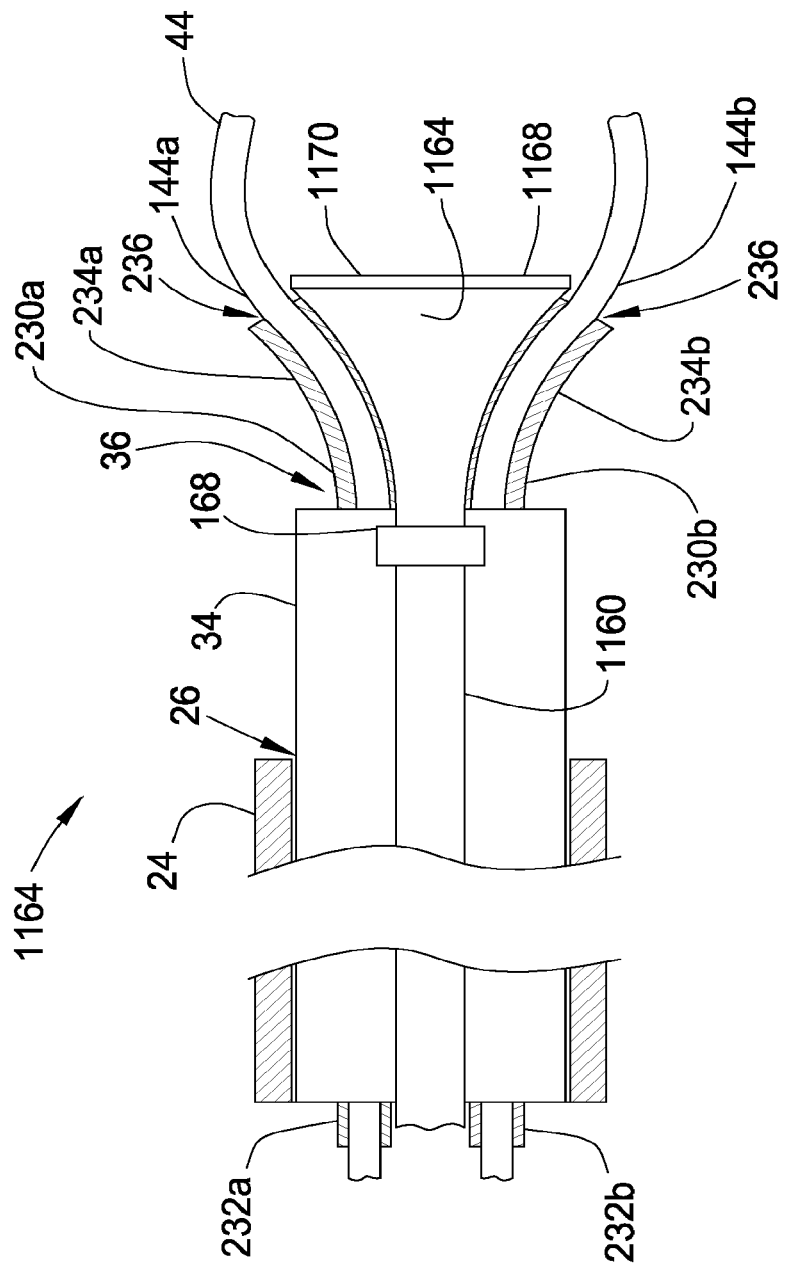
FIG. 15 is a top, partial cut-away view of the device distal end showing the inner member distal end, in accordance with another embodiment.

FIG. 15 is a top, partial cut-away view of the device distal end 16 showing the inner member distal end 34, in accordance with another embodiment. The tissue severing device 10 further comprises two cutting element sleeves 230a,b. Each cutting element sleeve 230a,b comprises an elongated body having a cutting element sleeve proximal end 232a,b extending through the inner member lumen 36 and into the handle 50 and a cutting element sleeve distal end 234a,b opposite the cutting element sleeve proximal end 232a,b. Each of the two cutting element sleeves 230a,b further comprises a sleeve lumen 236a,b that extends from the cutting element sleeve proximal end 232a,b to the cutting element sleeve distal end 234a,b therethrough. The cutting element portions 144a, 144b of the cutting element distal end 44 are operable to be received within the sleeve lumen 236a,b.

The two cutting element sleeves 230a,b spread apart from each other under the urging engagement of one or more of the spring bias of the cutting element 44 and the cutting element engagement element 1170 of the slidable support ribbon distal end 1164. In the case of the cutting element engagement element 1170, the cutting element engagement element 1170 engages the two cutting element sleeve distal ends 234a,b about the cutting element portions 144a, 144b of the cutting element distal end 44 effectively assisting in spreading apart the cutting element portions 144a, 144b and thus opening or making more circular the loop formed by the cutting element distal end 44, the two cutting element sleeves 230a,b preventing direct contact between the cutting element engagement element 1170 and the cutting element portions 144a, 144b.

Figure 16:
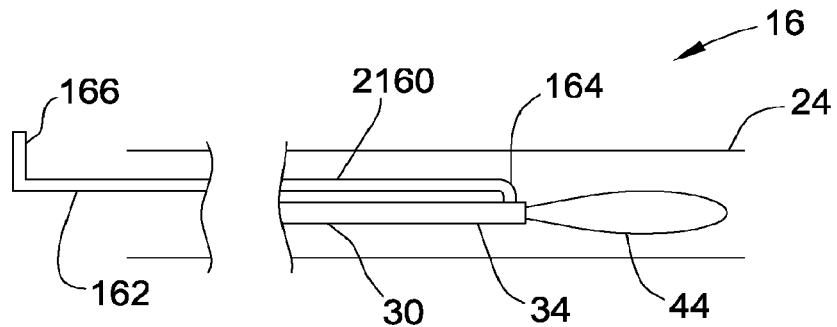
FIG. 16 is a side view of the device distal end showing a slidable support ribbon wherein the slidable support ribbon distal end is fixedly coupled to the inner member distal end, in accordance with an embodiment.

FIG. 16 is a side view of the device distal end 16 showing a slidable support ribbon 2160 wherein the sliding support ribbon distal end 164 is fixedly coupled to the inner member distal end 34, in accordance with an embodiment. When the inner member distal end 34 is exposed by the withdrawing tube member distal end 24, the user may pull the sliding support ribbon proximal end 162 in the proximal direction so as to flex the inner member distal end 34 into a desired curve to present the cutting element distal end 44 at an angle alpha to the tube member axis X. The user may control the sliding support ribbon distal end 164 in a desired position by pulling or pushing a snare 166 at the sliding support ribbon proximal end 162. It is appreciated that the slidable support ribbon 2160 may also be moved proximally and distally by the apparatus presented for the other embodiments herein or by apparatus known in the art.

As previously discussed, the cutting element 40 is operable for cutting and severing tissue. The cutting element 40 comprises a cutting element proximal end 42 that engages the inner member 30 and a cutting element distal end 44, at least a portion of which is used to cut and sever tissue.

Various embodiments of the cutting element proximal end 42 are anticipated. In general, embodiments of the cutting element proximal end 42 are anticipated that either couple with the inner member distal end 34 or pass through the inner member 30 to couple with other elements within the handle 50. It is appreciated that there are many coupling elements that may be used to provide fixed or removable coupling between the inner member distal end 34 and the cutting element proximal end 42.

Figure 17:
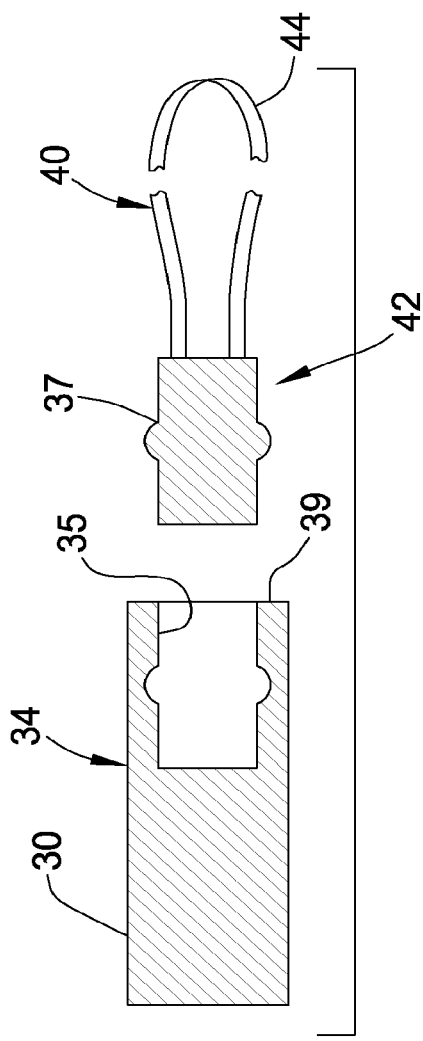
FIG. 17 is a side cross-sectional view of an embodiment of a cutting element proximal end and an inner member distal end that are operable for removable coupling engagement therebetween.

In accordance with an embodiment, a cutting element 40 is provided that may be removably coupled with the inner member distal end 34. FIG. 17 is a side cross-sectional view of an embodiment wherein the cutting element proximal end 42 and the inner member distal end 34 are operable for removable coupling engagement therebetween. The cutting element proximal end 42 comprises a mating element 37 and the inner member distal end 34 comprises a receiving element 35. The mating element 37 and the receiving element 35 are operable for removable coupling therebetween, wherein the mating element 37 is received and coupled to the receiving element 35.

In accordance with an embodiment, a plurality of cutting elements 40 may be provided, each suitable for a particular purpose such that one cutting element 40 may be interchanged on the inner member distal end 34 with another cutting element 40 of a same or different configuration. By way of example, cutting elements 40 of differing sizes and shapes may be provided suitable for a particular purpose. Further, as the cutting element 40 becomes dull, a replacement cutting element 40 may replace the first.

In accordance with other embodiments, a cutting element 40 is provided that comprises a cutting element proximal end 42 that passes through the inner member 30 and is operable for coupling with elements within the handle 50. FIG. 18 is a side, cut-away view of an inner member 30 further comprising at least one inner member lumen 36 that extends from the inner member proximal end 32 to the inner member distal end 34 therethrough. In accordance with the embodiment of FIG. 18, the cutting element 40 comprises an elongated member that forms a contiguous element that defines a loop 46 at the cutting element distal end 44 and two ends 48 at the cutting element proximal end 42. In accordance with an embodiment, the cutting element 40 is a wire. In another embodiment, the cutting element 40 is a ribbon, that is, a flat-sided elongated member that defines a loop 46 at the cutting element distal end 44 with the two ends 48 of the ribbon forming the cutting element proximal end 42. The cutting element proximal end 42 is operable to be received within the inner member lumen 36 and extend from the inner member proximal end 32 suitable for a particular purpose discussed below.

Various embodiments of the cutting element distal end 44 are anticipated. In accordance with an embodiment, the cutting element distal end 44 comprises a blade that is operable for cutting and severing tissue. In accordance with other embodiments, the cutting element distal end 44 comprises a loop 46, such as, but not limited to a loop of wire and ribbon. At least a portion of the cutting element distal end 44 comprises one or more sharp portions 45 that are suitable for severing tissue. FIG. 18 shows an embodiment of a cutting element distal end 44, in accordance with an embodiment. The cutting element distal end 44 comprises a wire in the form of a loop 46 including a sharp edge 45 that is preferentially sharp so as to cut tissue. The sharp edge 45 is operable such that it may cut into adjacent tissue as it is released by the tube member distal end 24 and as the tissue severing device 10 is pulled proximally toward the user.

Figure 19A:
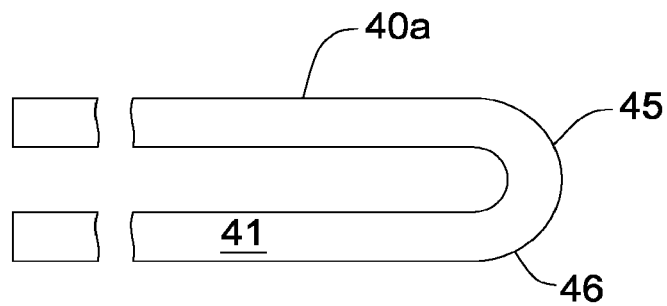
FIG. 19A is a top view of an embodiment of a cutting element, in accordance with an embodiment.

FIG. 19A is a top view showing an embodiment of a cutting element 40a, in accordance with an embodiment. The cutting element distal end 44 comprises a ribbon in the form of a loop 46 including a sharp edge 45 that is preferentially sharp so as to cut tissue. A broad surface 41 of the cutting element 40a is generally parallel to a plane defined by the loop 46 so as to present the sharp edge 45 also generally parallel with the plane defined by the loop 46.

Figure 19B:
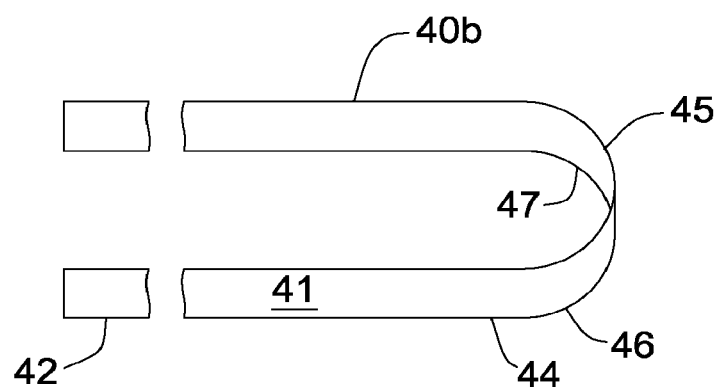
FIG. 19B is a perspective view of an embodiment of a cutting element, in accordance with an embodiment.

FIG. 19B is a perspective view showing an embodiment of a cutting element 40b, in accordance with an embodiment. The cutting element distal end 44 comprises a ribbon in the form of a loop 46 including a sharp edge 45 that is preferentially sharp so as to cut tissue, and a dull edge 47 that is not sharp relative to the sharp edge 45, such that it may not cut tissue. A broad surface 41 of the cutting element 40b is generally perpendicular to a plane defined by the loop 46 so as to present the sharp edge 45 also generally perpendicular with the plane defined by the loop 46.

The sharp edge 45 is operable to cut into adjacent tissue as it is released by the tube member distal end 24, as shown in FIG. 11B, and as the tissue severing device 10 is pulled proximally toward the user. The sharp edge 45 is presented on the edge of the cutting element distal end 44 that faces proximally when it is released by the tube member distal end 24. In other embodiments, the sharp edge 45 may comprise serrations so as to assist in severing tissue.

Various sizes and configurations of embodiments of the cutting element distal end 44 are anticipated. In the embodiment of FIG. 3, the cutting element distal end 44 is operable to fit within the tube member lumen 26 without elastic deformation of the cutting element distal end 44.

In the embodiment of FIGS. 5A-5B, the cutting element distal end 44 comprises a substantially elastic material such that the loop 46 may have a diameter somewhat larger than the inner diameter of the tube member lumen 26. When the tube member distal end 24 is advanced in the distal direction, the cutting element distal end 44 is operable to substantially elastically deform and be slidingly received within the tube member lumen 26 as shown in FIG. 5A. When the tube member distal end 24 is advanced in the proximal direction, the cutting element distal end 44 is operable to exit the tube member lumen 26 and substantially elastically expand therefrom. In accordance with an embodiment, the cutting element distal end 44 is in the form of a substantially oval loop 46 when released from the tube member lumen 26. The loop 46 is operable to be biased to open up when the tube member distal end 24 is withdrawn therefrom. When the tube member 20 is advanced over the cutting element distal end 44, the cutting element distal end 44 is operable to elastically deform under the impinging force of the tube member distal end 24 into a substantially closed or pinched-down oval shape so as to enter the tube member lumen 26. In accordance with an embodiment, and by way of example and not limited thereto, the loop 46 of the cutting element distal end 44 may have a diameter of about 12 mm, wherein the tube member may have an inner diameter of about 5 mm.

It is appreciated that the cutting element 40 may be constructed from many typed of materials, such as, but not limited to, stainless steel and shape-memory metals or metal alloys such as, but not limited to, nickel-titanium alloy.

In accordance with an embodiment, the cutting element distal end 44 is substantially uniformly elastically deformable. In accordance with other embodiments, the cutting element distal end 44 comprises one or more elastic regions operable to provide elastic deformation of the cutting element distal end 44.

Figure 19C:
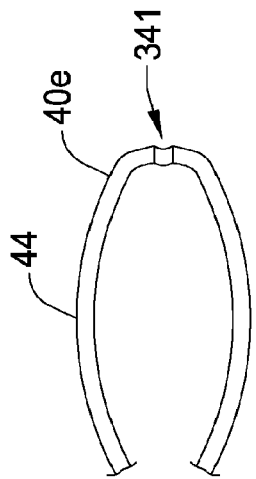
FIGS. 19C and 19D are top views, expanded and compresses, respectively, of an embodiment of a cutting element, in accordance with an embodiment.
Figure 19E:
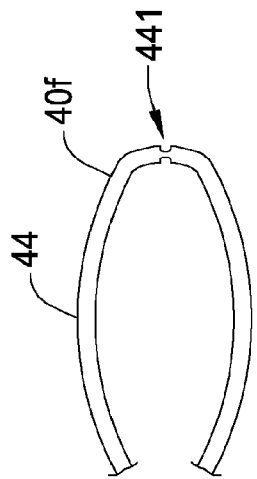
FIG. 19E is a top view showing an embodiment of a cutting element, in accordance with an embodiment.
Figure 19D:
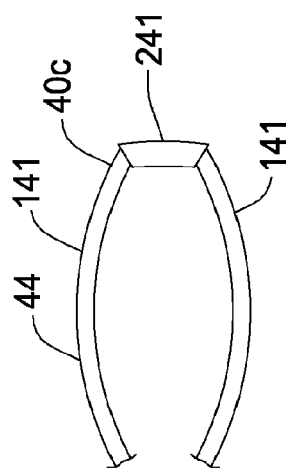

In accordance with an embodiment, the cutting element distal end 44 is formed as a single element. In accordance with another embodiment, the cutting element distal end 44 may be formed by integrating or joining separate components comprising one or more materials, at least some of which have elastic properties. FIGS. 19C and 19D are top views showing an embodiment of a cutting element 40c, in accordance with an embodiment. The cutting element distal end 44 comprises a ribbon in the form of a loop 46 comprising two stainless steel portions 141 coupled together by a super-elastic nickel-titanium alloy portion 241, wherein the nickel-titanium portion 241 provides a significant portion of the elasticity of the cutting element distal end 44 to a collapsed shape as shown in FIG. 19C and the stainless steel portions 141 providing generally the bias to the expanded shape as shown in FIG. 19D.

It is also appreciated that the cutting element 40 may be constructed with geometric features that assist in forming a loop at the cutting element distal end 44. FIG. 19E is a top view showing an embodiment of a cutting element 40e, in accordance with an embodiment. The cutting element distal end 44 comprises a ribbon defining a crease 341 across the width of the ribbon. The crease 341 is operable to allow for preferential bending to assist in compressing the cutting element distal end 44 into an elongated loop for the cutting element distal end 44 to be received within the tube member lumen 26.

Figure 19F:
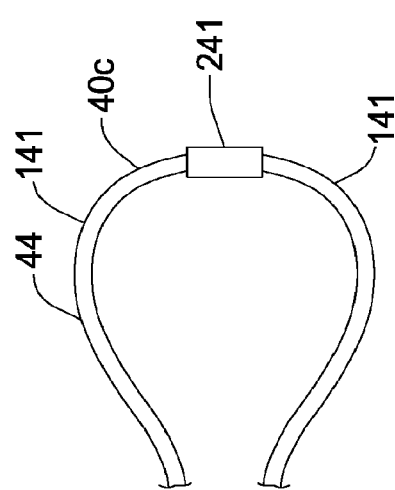
FIG. 19F is a top view showing another embodiment of a cutting element, in accordance with an embodiment.

FIG. 19F is a top view showing another embodiment of a cutting element 40f, in accordance with an embodiment. The cutting element distal end 44 comprises a ribbon defining a necked-down portion 441. The necked-down portion 441 is operable to allow for preferential bending to assist in compressing the cutting element distal end 44 into an elongated loop for the cutting element distal end 44 to be received within the tube member lumen 26.

Figure 20:
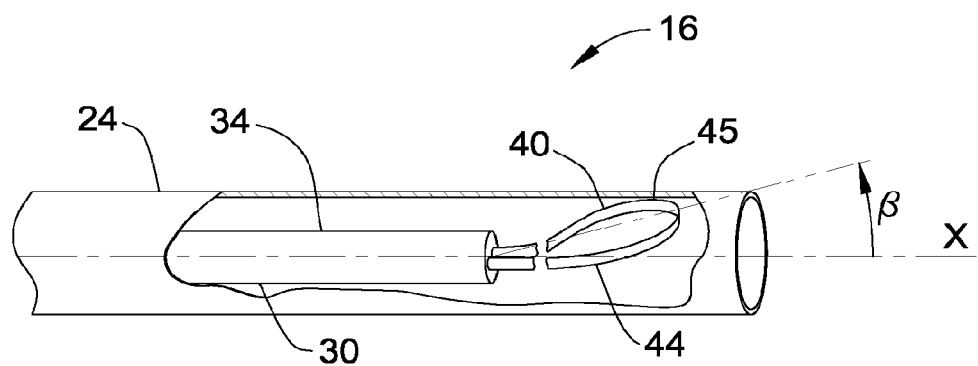
FIG. 20 is a side partial cut-away view of the device distal end wherein the cutting element distal end has a bias to an angle beta to the tube member axis, in accordance with an embodiment.

FIG. 20 is a side partial cut-away view of the device distal end 16 wherein the cutting element distal end 44 has a bias to an angle beta to the tube member axis X, in accordance with an embodiment. The bias of the cutting element distal end 44 is operable such that the sharp edge 45 is presented to tissue when the device distal end 16 is placed along side and adjacent to tissue to be severed as will be discussed below. In accordance with this embodiment, the tissue may begin to be severed prior to the emergence of the inner member distal end 34 from the tube member distal end 24.

In accordance with an embodiment, the inner member 30 and thus the cutting element 40 may be operable to be assembled in the tube member lumen 36 such that the cutting element distal end 44 may be retained at one or more predetermined angles with respect to the handle 50. By way of example, in accordance with an embodiment, the cutting element distal end 44 may be operable to be assembled to extend from the tube member distal end 24 at one of four directions, such as up, right, down, or left, as viewed along the tube member axis X from the handle 50.

Figure 21:
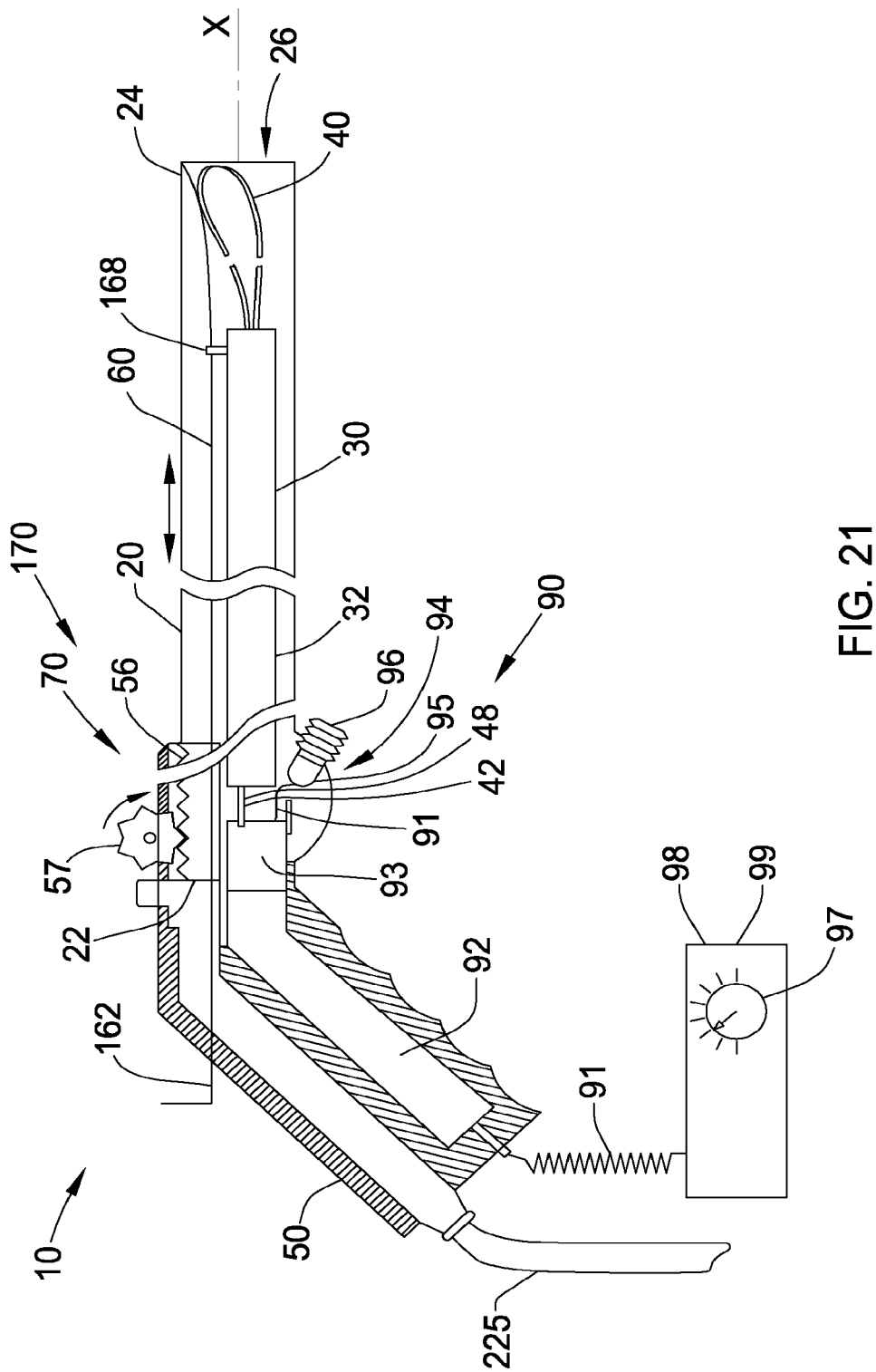
FIG. 21 is a side cut-away view of a tissue severing device in accordance with an embodiment.

In accordance with embodiments of the tissue cutting device 10, an energy source is provided to assist the cutting element proximal end 44 in cutting and severing tissue. FIG. 21 is a side partial cut-away view of a tissue severing device 10 comprising an energy source 90, in accordance with an embodiment. The cutting element proximal end 42 comprises two ends 48, such as shown in the embodiment of FIG. 18. The cutting element proximal end 42 extends through the inner member lumen 36 to the handle 50. Within the handle 50, the two ends 48 of the cutting element proximal end 42 are coupled to the energy source 90 operable to assist in severing tissue. It is appreciated that the energy source 90 may employ one or more energy modes that are operable to assist in cutting and severing tissue, such as, but not limited to, mechanical, radio frequency, thermal, ultrasonic, and any other suitable energy.

In accordance with an embodiment, the energy source 90 is a radio frequency energy source 90, and the cutting element 40 may function as a component of a monopolar or a bipolar system. The radio frequency energy source 90 may be operable as an electrocautery instrument so as to provide, among other things, coagulation of small bleeding vessels that may be encountered during the severing process.

In accordance with another embodiment, the two ends 48 of the cutting element proximal end 42 are coupled to an energy source 90 that is mechanical in operation. In accordance with an embodiment, the energy source 90 is an ultrasonic source that is operable to impart a vibratory action to the cutting element distal end 44 to assist in severing the tissue. In another embodiment, the energy source 90 is a mechanical oscillator that is operable to rapidly and alternatively pull on the two ends 48 of the cutting element proximal end 42 so as to impart a sawing motion to the cutting element distal end 44 to assist in severing the tissue.

In another embodiment, the energy source 90 is a mechanical oscillator, such as, but not limited to, a motor, that is operable to rapidly and alternatively push-pull on the two ends 48 of the cutting element proximal end 42 so as to provide a rapid in and out movement of the cutting element distal end 44 to assist in severing tissue.

In accordance with another embodiment, the inner member lumen 36 comprises a track that is operable to guide the movement of the cutting element distal end 44 which is coupled to a trolley that is adapted to couple with the track.

In yet another embodiment, the energy source 90 is a thermal source that is operable to heat the cutting element distal end 44 to assist in severing the tissue.

In accordance with embodiments wherein the cutting element proximal end 42 couples with the inner member distal end 34, the cutting element distal end 44 may be energized with energy by coupling the energy source 90 to the inner member proximal end 32. The energy from the energy source 90 is communicated to the cutting element distal end 44 via the inner member 30. It is appreciated that many energy sources may be used to communicate energy to the cutting element distal end 44 via the inner member 30. It is also appreciated that a mechanical energy source may be particularly effective. In accordance with an embodiment, the inner member proximal end 32 is coupled to a mechanical oscillator that is operable to rapidly push-pull on the inner member proximal end 32 so as to impart motion to the cutting element distal end 44 to assist in severing the tissue. In accordance with an embodiment, the energy source 90 is an ultrasonic source that is operable to impart a vibratory action to the inner member 30 that is communicated to the cutting element distal end 44 to assist in severing tissue.

In accordance with and embodiment, by way of example, the energy source 90 is a variable speed drive operable to induce oscillatory motion to the cutting element distal end 44 either directly or via the inner member 30. Referring again to FIG. 21, the drive includes a motor 92, a transmission 93, and a switch 94. The switch 94 comprises a first contact 95 housed in the handle 50 adjacent a button contact 96.

When the button contact 96 is in an initial position, the switch 94 represents an open electrical circuit. Thus, no current is supplied to the motor 92, and the cutting element distal end 44 is stationary. The motor 92 is electrically connected to power via the switch 94 and a control 99 when the button contact 96 is in the inward most position so as to make electric coupling with the first contact 95, as will be described more fully hereafter.

The control 99 includes a rotary pot 97 operable to allow a user to control the power available to the motor 92 and, thus, the speed of the cutting element distal end 44. Appropriate lengths of electrical conductors 91 electrically interconnect the control 99, the switch, 94, and the motor 92.

The button contact 96 nests within a track (not shown) defined by the handle 50. A button return spring (not shown), which may be mounted between the button contact 96 and a portion of the handle 50, biases the button contact 96 in an outward position away from the first contact 95 and out of electrical communication therewith. The transmission 93 is operable to convert rotational motion from the motor 92 to an oscillatory motion that is communicated to the cutting element distal end 44 by coupling the transmission 93 to either the cutting element proximal end 42 or the inner member proximal end 32.

In accordance with embodiments of the tissue cutting device 10, and referring to FIGS. 1A and 1B, the tissue cutting device 10 further comprises an engagement means 70 being operable for moving the tube member 20 proximally and distally over the inner member 30. It is anticipated that there are many engagement means 70 that may be used to provide the function for moving the tube member 20 proximally and distally, including unpowered, powered, manual and automatic means, some of which will be described further below. In accordance with an embodiment, wherein the handle 50 comprises the engagement means 70 as a slidable engagement element, and the tube member 20 is operable to be moved proximally and distally over the inner member 30 by a user grasping the tube member 20 and sliding the tube member 20 through the slidable engagement element within the handle 50.

The tissue severing device 10, shown in FIGS. 1 and 21, further comprises an engagement means 70 in the form of a tube member moving element 170 operable to engage the tube member proximal end 22 for moving the tube member 20 proximally and distally over the inner member 30. In accordance with an embodiment as shown in FIG. 21, the tube member moving element 170 that is operable for axially moving the tube member 20 includes a rack 56 and pinion 57. It is understood that there are many rack and pinion configurations in the art suitable for a particular purpose. For example, but not limited thereto, in accordance with an embodiment, the rack 56 comprises a plurality of spaced notches or grooves located at the tube member proximal end 22. The rack 56 may be an integral feature of the tube member 20 or an element that is coupled to the tube member proximal end 22. The pinion 57 comprises an engagement wheel having teeth that operably engage the spaced notches of the rack 56. In operation, when the pinion 57 is rotated in a clockwise direction, the rack 56 is engaged to advance the tube member 20 axially in a proximal direction. When the pinion 57 is rotated in the opposite direction, the rack 56 is engaged to move the tube member 20 axially in a distal direction.

A tube member moving element 170 for axially moving the tube member 20 relative to the inner member 30 and cutting element 40 may be provided by many known means, such as, but not limited to a rack and pinion drive system wherein the pinion comprises helical threads and is operable by rotating the pinion along the tube member axis X, such as shown in the embodiment of FIGS. 1A and 1B. Other linear actuators may also be used, suitable for a particular purpose. It is appreciated that the tube member moving element 170 may be electrically and manually operated.

It is appreciated that the tube member moving element 170 for axially moving the tube member 20 relative to the inner member 30 and cutting element 40 may be operably coupled to the energy source 90 for energizing the cutting element distal end 44. By way of example, but not limited thereto, in accordance with an embodiment, the energy source 90 for energizing the cutting element distal end 44 is activated only when the tube member 20 has been moved proximally by a predetermined amount. Such a configuration may prevent the activation of the energy source 90 prior to the withdrawal of the cutting element distal end 44 from the cutting element distal end 44.

It is appreciated that other elements may be incorporated into the tissue severing device 10. By way of example, but not limited thereto, the tube member 20 may include one or more accessory lumens such as, but not limited to, for suction, irrigation, inflation. Gas, liquid, or a combination thereof from an external source may be administered through a communications lumen 225, shown in FIG. 21, and coupled to the tube member lumen 26 at the tube member proximal end 22. For example, but not limited thereto, an aqueous solution may be employed for irrigation purposes or a local anesthetic, such as lidocaine, may be administered through the tube member lumen 26 so as to exit the tube member distal end 24. In addition, the tube member lumen 26 may be operatively connected to an external vacuum source. The external vacuum source may provide suction to, for example, but not limited to, remove from the patient, fluids, such as, but not limited to, blood, irrigation fluid or smoke generated during use of the cutting element 40 or other device.

Figure 23:
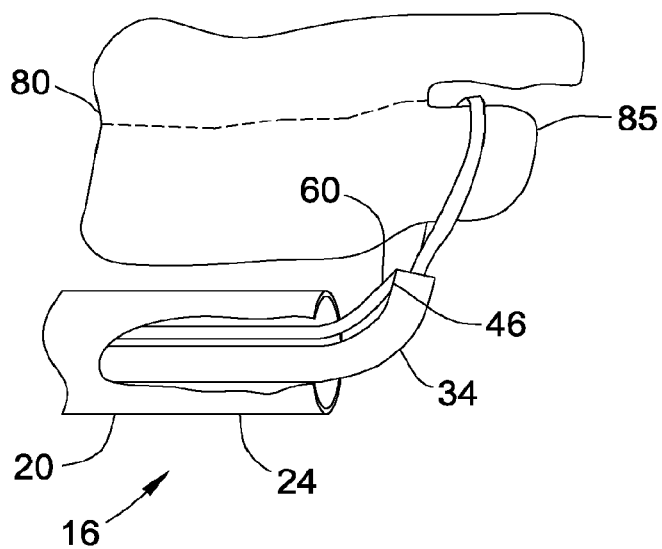
FIG. 23 is a side view of the distal region of an embodiment of the tissue severing device as cutting through tissue, in accordance with an embodiment.
Figure 22:
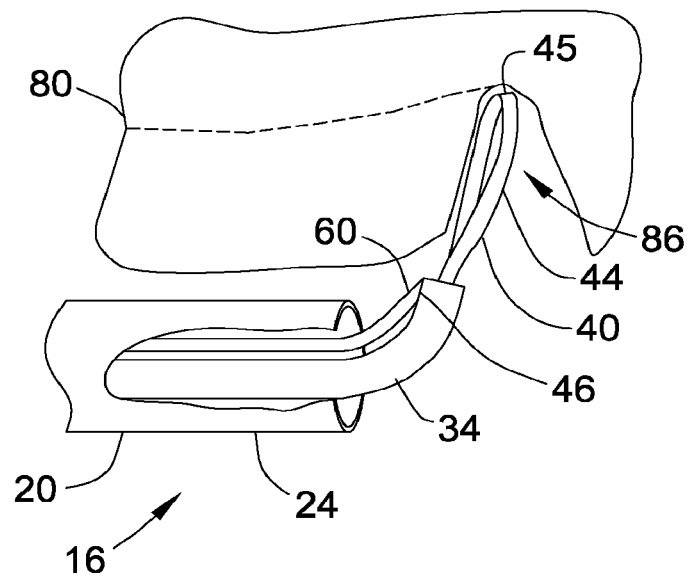
FIG. 22 is a side view of the distal region of an embodiment of the tissue severing device as presented to tissue, in accordance with an embodiment.

In using the tissue severing device 10 of an embodiment shown in FIG. 21, the cutting element 40 and inner member 30 are first contained within the tube member lumen 26 of the tube member 20. The tube member distal end 24 may be passed through a trocar sleeve that has been placed within a patient and placed along side and adjacent to tissue 80 to be severed as shown in FIG. 22. FIG. 22 is a side view of the device distal end 16 placed along side tissue 80 to be severed. The tube member 20 is moved axially proximally so as to withdraw from and expose the cutting element distal end 44 and the inner member distal end 34. The cutting element distal end 44 is operable to impinge and cut into the adjacent tissue 80 substantially laterally or laterally and proximally (toward the handle 50) so as to create an arc-shaped cut 86 into the tissue 80, as shown in FIG. 22. Once the cutting element 40 is exposed the desired amount, the handle 50, as shown in FIG. 1B, is pulled proximally so as to pull the extended cutting element distal end 44 through the tissue 80, severing the tissue 80, with the severed tissue 85 extruding through the loop 46 of the cutting element distal end 44, as shown in FIG. 23.

The support ribbon 60 substantially prevents the inner shaft distal end 34 from extending distally toward the tube member axis X during the cutting operation as well as prevents the cutting element distal end 44 from cutting too deeply. The support ribbon 60 guides the tissue 80 into the loop 46 of the cutting element distal end 44 and therefore limits the depth of the cut 86. Were the cutting element distal end 44 to cut too deeply, the cutting element distal end 44 may get stuck during the cutting operation. Severed tissue 85 may be removed from the patient by another device.

Additional severing operations may be performed by moving the exposed cutting element distal end 44 to another portion of tissue 80 to be severed and impinging the cutting element distal end 44 into the tissue 80. Alternatively, after each cutting operation, the tube member 20 may thereafter be moved distally so as to advance over the inner member distal end 34 and the cutting element distal end 44. The tube member distal end 24 is again placed along side tissue 80 to be severed and the process is repeated.

It is appreciated that the angle of the cutting element distal end 44 to the tissue 80 may be changed by the selective positioning of the tube member distal end 24 with respect to the cutting element distal end 44 or the inner member distal end 34. The user may adjust the angle of the cutting element distal end 44 at any time during the cutting operation so as to control the cutting operation. By way of example, but not limited thereto, less tissue 80 may be severed by reducing the exposure of the cutting element distal end 44. By way of another non-limiting example, the initiation of the cutting operation may be done at first by limiting the exposure of the cutting element distal end 44 and subsequently increasing the exposure of the cutting element distal end 44 as the tissue severing device 10 is pulled proximally during the cutting operation.

It is appreciated that by virtue of the cutting element distal end 44 being operable to impinge and cut into the adjacent tissue 80 substantially laterally or combination laterally and proximally (toward the handle 50) so as to create an arc-shaped cut 86 into the tissue 80, the cutting element distal end 44 may be placed and the cut initiated closer to vital organs and tissue that is to remain unsevered. In embodiments of the tissue severing device 10 disclosed herein, the uterus may be morcellated while the uterus is still attached to the cervix. The lateral cutting action of the embodiments of the tissue severing device 10 greatly reduce the risk of injuring adjacent tissue and organs as compared with uterus amputation procedures, particularly for those embodiments of the tissue severing device 10 that do not incorporate heat in the cutting operation. Further, since no amputation of the uterus prior to morcellation is required, only one device, the tissue severing device 10, is required for both the separation of the uterus from the cervix and morcellating the uterus for removal, reducing the cost and complexity of the surgery. It is evident that embodiments of the tissue severing device 10 disclosed herein presents a significant improvement over prior art devices, as, among other things, downward (distal) traction is not employed and uterus amputation and the corresponding amputation surgical device is not required.

It may be necessary for the surgeon to rest the device distal end 16 in the patient while other operations are performed. The tube member 20 may be moved distally so as to advance over the inner member distal end 34 and the cutting element distal end 44 so as to prevent the cutting element distal end 44 from injuring the patient while resting in the patient.

Figure 24:
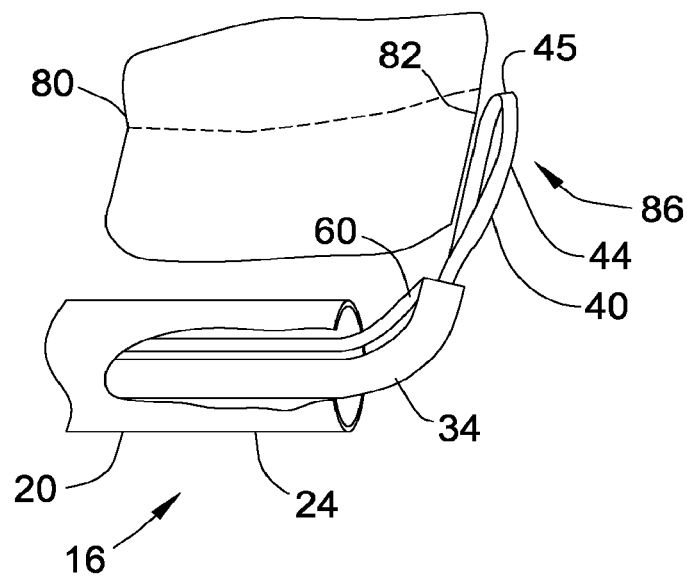
FIG. 24 is a side view of the distal region of an embodiment of the tissue severing device as presented to tissue, in accordance with an embodiment

In accordance with another method of using the tissue severing device 10, the tube member distal end 24 is moved proximately so as to withdraw from the cutting element distal end 44 and the inner member distal end 34. The cutting element distal end 44 is placed beyond a leading edge 82 of the tissue 80 with the sharp portion 45 of the cutting element distal end 44 placed adjacent tissue 80 to be severed, as shown in FIG. 24. Cutting of the tissue 80 is affected by pulling proximally on the tissue severing device.

Referring again to the ability of the inner member distal end 34 to deform or flex from a substantially straight configuration to a curved or angled configuration, it is appreciated that articulation apparatus operable to allow for articulation of the inner member distal end 34 may be provided by many apparatus, such as, but not limited to, nested ring sections, sliding corrugated sections, pivots, movable joints, and extensible tubing, such as, but not limited to, bellows-type tubing.

It is also appreciated that means for providing control of, movement of, and/or a bias to the segments into a predetermined configuration, such as substantially straight or to form a curve of a predetermined angle, may be provided by many apparatus, such as, but not limited to, elastic elements, such as, but not limited to, springs and spine members, and mechanical elements, such as, but not limited to, a slidable support ribbon 165 and pull-wires and rods.

Figure 25:
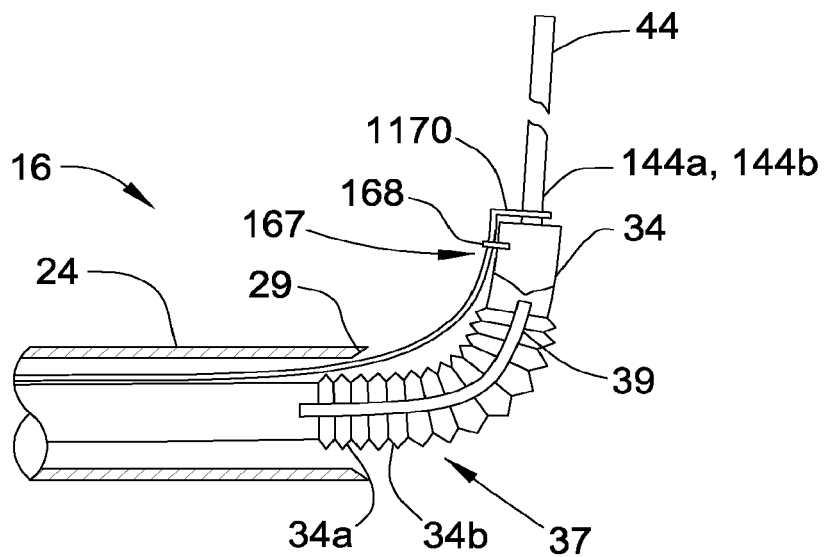
FIG. 25 is a perspective view of a device distal end including an inner member distal end that is operable to allow for articulation, in accordance with an embodiment.

FIG. 25 is a perspective view of a device distal end 16 including an inner member distal end 34 that is operable to allow for articulation, in accordance with an embodiment. At least a portion of the inner member distal end 34 comprises two or more segments 34a, 34b that are interconnected by a bellows joint 37 supported by one or more spine members 39. The one or more spine members 39 may be operable to provide a predetermined bias on the segments 34a, 34b, so as to present the inner member distal end 34 in a straight or curved configuration suitable for a particular purposes.

Figure 26:
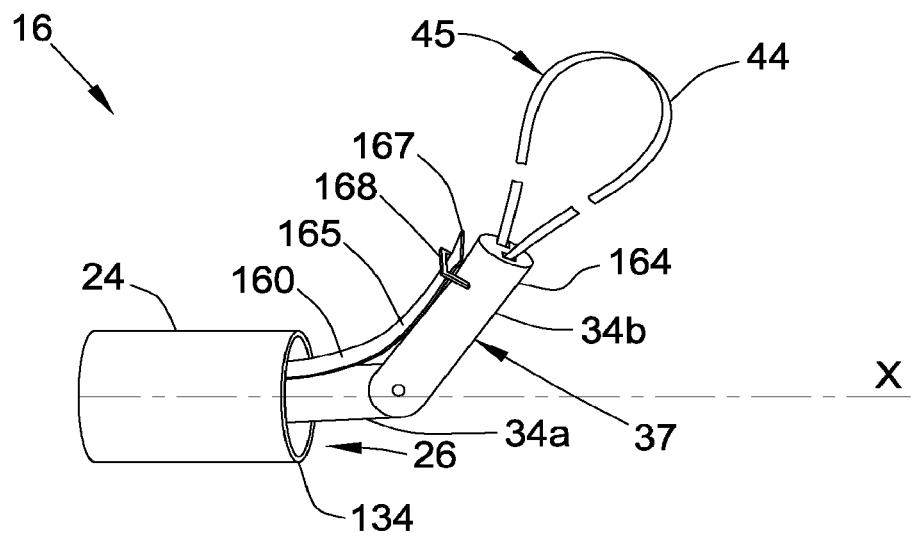
FIG. 26 is a perspective view of a device distal end including another inner member distal end that is operable to allow for articulation, in accordance with an embodiment.

FIG. 26 is a perspective view of a device distal end 16 including another inner member distal end 34 that is operable to allow for articulation, in accordance with an embodiment. At least a portion of the inner member distal end 34 comprises two or more segments 34a, 34b that are interconnected by a pivot joint 37. The movement of the pivot joint 37 may be controlled, at least in part, by the engagement of the slidable support ribbon 165 with the engagement ring 168 so as to present the inner member distal end 34 in a straight or curved configuration. The pivot joint 37 is located between the inner member proximal end 32 and the engagement ring 168.

It is appreciated that the tube member distal end 24 may have a tube flare portion 29 to guide the engagement of the slidable support ribbon 165 and/or the inner member distal end 34 as shown in FIG. 25. The tube flare portion 29 is operable to provide a smooth bend radius for the components that may engage it.

In operation, when the tube member distal end 24 is advanced over the cutting element distal end 44, the slidable support ribbon 165 and the inner member distal end 34 lie substantially parallel with each other within the tube member distal end 24. As the tube member distal end 24 is withdrawn, the cutting element distal end 44 expands into an open position. As the tube member distal end 24 is further withdrawn, the cutting element engagement element 1170 engages the cutting element portions 144a, 144b of the cutting element distal end 44 to stabilize, or hold-open, the cutting element distal end 44 during subsequent tissue severing. The flared portion 167 of the slidable support ribbon distal end 164 engages the engagement ring 168 reducing any further traction on the cutting element distal end 44 by the cutting element engagement element 1170. The crease 1141 preferentially bends so as to reduce engagement of the slidable support ribbon distal end 164 on the tube member distal end 24.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

I claim:
1. A tissue severing device comprising:
a handle;

a tube member including an elongated tube having a tube member proximal end extending into the handle and a tube member distal end opposite the tube member proximal end, the tube member defining a tube member lumen that extends through the tube member proximal end to the tube member distal end and defining a tube member axis;

an inner member including an elongated body having an inner member proximal end extending through the tube member lumen and into the handle and an inner member distal end opposite the inner member proximal end, the inner member being operable to be received within the tube member lumen;

a cutting element including a cutting element proximal end and a cutting element distal end opposite the cutting element proximal end, the cutting element proximal end extending into the inner member distal end, the cutting element distal end extending from the inner member distal end, the tube member distal end being operable to move distally over and receive the inner member distal end and the inner member distal end therein, and the tube member distal end being operable to move in a proximal direction to expose the cutting element distal end; and a slidable support ribbon operable for supporting the inner member distal end in a curved position when the inner member distal end is at least partially exposed by the withdrawal of the tube member distal end, the slidable support ribbon comprising an elongated body including a slidable support ribbon proximal end and a slidable support ribbon distal end opposite the slidable support ribbon proximal end, the slidable support ribbon proximal end extending through the tube member lumen from about the tube member proximal end to the tube member distal end and adjacent the inner member, the slidable support ribbon distal end being fixedly coupled to the inner member distal end and operable such that when the inner member distal end is exposed by the withdrawing tube member distal end, a user may pull the slidable support ribbon proximal end in the proximal direction so as to flex the inner member distal end into a desired curve to present the cutting element distal end at an angle to the tube member axis.

2. The tissue severing device of claim 1, wherein the slidable support ribbon distal end is operable to substantially prevent the inner member distal end from extending toward the tube member axis when the cutting element distal end is pulled through tissue to be severed, the slidable support ribbon is operable to control the depth of cut into the tissue by guiding tissue into the cutting element distal end.

3. The tissue severing device of claim 1, wherein the slidable support ribbon proximal end extends from the handle such that the slidable support ribbon proximal end may be grasped by a user.

4. The tissue severing device of claim 1, wherein the slidable support ribbon proximal end and the handle comprises an engagement element such that the slidable support ribbon proximal end may be releasably coupled to the handle when the slidable support ribbon is extended or retracted to a desired position, the engagement element operable for temporarily fixating the position of the slidable support ribbon proximal end.

5. The tissue severing device of claim 1, wherein the cutting element comprises a cutting element proximal end and a cutting element distal end opposite the cutting element proximal end, the cutting element proximal end and the inner member distal end removably coupled therebetween, the cutting element distal end including at least a portion operable to cut and sever tissue.

6. The tissue severing device of claim 5, the cutting element proximal end comprising a mating element and the inner member distal end comprising a receiving element, the mating element and the receiving element are removably coupled therebetween.

7. The tissue severing device of claim 1, wherein the cutting element distal end defines a loop, at least a portion of the cutting element distal end including one or more sharp portions that are suitable for severing tissue.

8. The tissue severing device of claim 7, wherein the loop is operable to be biased to expand when the tube member distal end is withdrawn therefrom, and wherein the cutting element distal end being elastically deformed under the impinging force of the tube member distal end so as to enter and be contained by the tube member lumen when the tube member is advanced over the cutting element distal end.

9. The tissue severing device of claim 1, wherein the cutting element distal end has a bias to form an angle to the tube member axis.

10. The tissue severing device of claim 1, wherein the cutting element comprises a wire.

11. The tissue severing device of claim 1, wherein the cutting element distal end comprises a ribbon defining a loop including a sharp edge that is preferentially sharp operable to cut tissue, and a dull edge operable to not cut tissue.

12. The tissue severing device of claim 1, wherein the inner member further comprises at least one inner member lumen extending through the inner member proximal end and the inner member distal end, the cutting element proximal end extending through the inner member lumen and coupled within the handle.

13. The tissue severing device of claim 12, wherein the cutting element comprises a ribbon defining a flat-sided elongated member that defines a loop at the cutting element distal end and two ends forming the cutting element proximal end, the cutting element proximal end received within the inner member lumen and extending from the inner member proximal end.

14. The tissue severing device of claim 1, further comprising an energy source coupled to the cutting element and operable to assist the cutting element proximal end in cutting and severing tissue.

15. The tissue severing device of claim 14, wherein the energy source is housed within the handle, wherein the inner member further comprises at least one inner member lumen extending through the inner member proximal end and the inner member distal end, wherein the cutting element comprises an elongated member that forms a contiguous element that defines a loop at the cutting element distal end and two ends at the cutting element proximal end, the cutting element proximal end extending through the inner member lumen to the handle and the two ends of the cutting element proximal end are coupled to the energy source.

16. The tissue severing device of claim 15, wherein the energy source is a mechanical oscillator that is operable to rapidly and alternatively pull on the two ends of the cutting element proximal end so as to impart a sawing motion to the cutting element distal end.

17. The tissue severing device of claim 14, wherein the energy source is operable to impart mechanical energy to the cutting element distal end.

18. The tissue severing device of claim 14, wherein the energy source is a radio frequency energy source, and the cutting element may function as a component of an electrical system.

19. The tissue severing device of claim 14, wherein the energy source is operable to impart a vibratory motion to the cutting element distal end.

20. The tissue severing device of claim 14, wherein the energy source is a thermal source that is operable to heat the cutting element distal end.

21. The tissue severing device of claim 14, wherein the energy source is coupled to the inner member proximal end, the energy from the energy source operable to be communicated to the cutting element distal end via the inner member.

22. The tissue severing device of claim 21, wherein the inner member proximal end is coupled to a mechanical oscillator that is operable to rapidly push-pull on the inner member proximal end so as to impart motion to the cutting element distal end.

23. The tissue severing device of claim 1, further comprising an engagement means operable for moving the tube member proximally and distally over the inner member.

24. The tissue severing device of claim 23, wherein the engagement means comprises a tube member moving element comprising a rack and pinion, the rack comprising a plurality of spaced notches coupled to the tube member proximal end, and the pinion comprising an engagement wheel having teeth that operably engage the spaced notches of the rack.

25. The tissue severing device of claim 23, wherein the engagement means is a slidable engagement element and the tube member is operable to be moved proximally and distally over the inner member by a user grasping the tube member and sliding the tube member through the slidable engagement element within the handle.

* * * * *